United States Patent

Lau et al.

[11] Patent Number: 5,876,432
[45] Date of Patent: Mar. 2, 1999

[54] SELF-EXPANDABLE HELICAL INTRAVASCULAR STENT AND STENT-GRAFT

[75] Inventors: Lilip Lau, Sunnyvale; Charles Thomas Maroney, Portola Valley; William M. Hartigan, Fremont; Woonza Rhee, Palo Alto; Kimberly A. McCullough, Hayward, all of Calif.

[73] Assignee: Gore Enterprise Holdings, Inc., Newark, Del.

[21] Appl. No.: 411,452

[22] Filed: Mar. 28, 1995

Related U.S. Application Data

[62] Division of Ser. No. 221,815, Apr. 1, 1994.
[51] Int. Cl.$^6$ ......................................................... A61F 2/06
[52] U.S. Cl. ................................. 623/1; 623/12; 606/191
[58] Field of Search .................................... 623/1, 11, 12; 606/191, 194, 198, 108

[56] References Cited

U.S. PATENT DOCUMENTS

| | | |
|---|---|---|
| 3,152,618 | 10/1964 | Rothermel et al. . |
| 3,174,851 | 3/1965 | Bueher et al. . |
| 3,351,463 | 11/1967 | Rozner et al. . |

(List continued on next page.)

FOREIGN PATENT DOCUMENTS

| | | |
|---|---|---|
| 0382014 | 8/1990 | European Pat. Off. . |
| 408245 | 1/1991 | European Pat. Off. . |
| 418677 | 3/1991 | European Pat. Off. . |
| 0472731 | 3/1992 | European Pat. Off. . |
| 0540290 | 5/1993 | European Pat. Off. . |
| 0556850 | 8/1993 | European Pat. Off. . |
| 0565251 | 10/1993 | European Pat. Off. . |
| 0 686 379 | 12/1995 | European Pat. Off. . |
| 196 17 823 A | 11/1997 | Germany . |
| 1 506 432 | 4/1978 | United Kingdom . |
| 1 567 122 | 5/1980 | United Kingdom . |
| 1 355 373 | 6/1994 | United Kingdom . |
| WO 88/06026 | 8/1988 | WIPO . |
| WO 90/04982 | 5/1990 | WIPO . |

(List continued on next page.)

OTHER PUBLICATIONS

Cragg, A.H., et al. "Percutaneous femoropopliteal graft placement" *Radiology*(1993) 187(3):643–648.
Cragg, A.H., et al. "Percutaneous femoropopliteal graft placement" *Journal of Vascular and Interventional Radiology*(1993) 4:455–463.
Cragg, A.H., et al. "Nitinol intravascular stent: Results of preclinical evaluation" *Radiology*(1993) 189:775–778.
Laborde et al. "Intralumianl bypass of abdominal aortic aneurysm: Feasibility study" *Radiology*(1992) 184:185–190.
MinTec™ Minimally Invasive Technologies Product Brochure for the Craggstent and Cragg EndoPro System 1, 4 pages total.
Schneider (USA) Inc., Pfizer Hospital Products Group, 5905 Nathan Ln., Minneapolis, Minnesota, 55442, Product Brochure for Catheters, Guidewires, and Stents, 2 pages total.
Products Brochure for Cook–Z™ Stents, Gianturco–Rosch Biliary Design, Cook®, A Cook Groups Company, P.O. Box 489, Bloomington, IN, 47402, U.S.A., 4 pages total.
Product Brochure for Palmaz™ Balloon–Expandable Stent, Johnson & Johnson Interventional Systems, 40 Technology Dr., P.O. Box 4917, Warren, NJ, 07059, 2 pages total.
Cragg et al., Nitinol Intravascular Stent: Results of Preclinical Evaluation; *Radiology*; pp. 775–778; Dec. 1993; vol. 189, No. 3.

*Primary Examiner*—Mary Beth Jones
*Attorney, Agent, or Firm*—Morgan & Finnegan, L.L.P.

[57] ABSTRACT

A device which includes at least a tubular stent member which if formed from a helically wrapped undulating member and a coupling member which extends through undulations of adjacent turns of the helically wrapped undulating member and is movable along the undulations, the device is foldable into a lumen deployable configuration and may also include a coaxially positioned graft member.

27 Claims, 10 Drawing Sheets

U.S. PATENT DOCUMENTS

| | | |
|---|---|---|
| 3,479,670 | 11/1969 | Medell . |
| 3,514,791 | 6/1970 | Sparks . |
| 3,562,820 | 2/1971 | Braun . |
| 3,625,198 | 12/1971 | Sparks . |
| 3,657,744 | 4/1972 | Ersek . |
| 3,710,777 | 1/1973 | Sparks . |
| 3,753,700 | 8/1973 | Harrison et al. . |
| 3,774,596 | 11/1973 | Cook . |
| 3,866,247 | 2/1975 | Sparks . |
| 3,866,609 | 2/1975 | Sparks . |
| 3,868,956 | 3/1975 | Alfidi et al. . |
| 3,927,422 | 12/1975 | Sawyer . |
| 3,949,073 | 4/1976 | Daniels et al. . |
| 3,953,566 | 4/1976 | Gore . |
| 3,974,526 | 8/1976 | Dardik et al. . |
| 4,130,904 | 12/1978 | Whalen . |
| 4,164,045 | 8/1979 | Bokros et al. . |
| 4,187,390 | 2/1980 | Gore . |
| 4,319,363 | 3/1982 | Ketharanathan . |
| 4,411,655 | 10/1983 | Schreck . |
| 4,424,208 | 1/1984 | Wallace et al. . |
| 4,425,908 | 1/1984 | Simon . |
| 4,488,911 | 12/1984 | Luck et al. . |
| 4,494,531 | 1/1985 | Gianturco . |
| 4,503,569 | 3/1985 | Dotter . |
| 4,512,338 | 4/1985 | Balko et al. . |
| 4,546,500 | 10/1985 | Bell . |
| 4,553,545 | 11/1985 | Maass et al. . |
| 4,557,764 | 12/1985 | Chu . |
| 4,580,568 | 4/1986 | Gianturco . |
| 4,582,640 | 4/1986 | Smestad et al. . |
| 4,604,762 | 8/1986 | Robinson . |
| 4,629,458 | 12/1986 | Pinchuk . |
| 4,641,653 | 2/1987 | Rockey . |
| 4,642,117 | 2/1987 | Nguyen et al. . |
| 4,647,416 | 3/1987 | Seiler, Jr. et al. . |
| 4,649,922 | 3/1987 | Wiktor . |
| 4,655,771 | 4/1987 | Wallsten . |
| 4,665,906 | 5/1987 | Jervis . |
| 4,689,399 | 8/1987 | Chu . |
| 4,733,665 | 3/1988 | Palmaz . |
| 4,738,666 | 4/1988 | Fuqua . |
| 4,739,762 | 4/1988 | Palmaz . |
| 4,740,207 | 4/1988 | Kreamer . |
| 4,760,849 | 8/1988 | Kropf . |
| 4,776,337 | 10/1988 | Palmaz . |
| 4,787,899 | 11/1988 | Lazarus ........................................ 623/1 |
| 4,798,606 | 1/1989 | Pinchuk . |
| 4,816,339 | 3/1989 | Tu et al. . |
| 4,820,298 | 4/1989 | Leveen et al. . |
| 4,830,003 | 5/1989 | Wolff et al. . |
| 4,842,575 | 6/1989 | Hoffman, Jr. et al. . |
| 4,856,516 | 8/1989 | Hillstead . |
| 4,886,062 | 12/1989 | Wiktor . |
| 4,886,500 | 12/1989 | Lazarus . |
| 4,913,141 | 4/1990 | Hillstead . |
| 4,957,508 | 9/1990 | Keneko et al. . |
| 4,969,458 | 11/1990 | Wiktor . |
| 4,990,151 | 2/1991 | Wallsten . |
| 4,990,155 | 2/1991 | Wilkoff . |
| 4,994,071 | 2/1991 | MacGregor ............................ 606/194 |
| 5,015,253 | 5/1991 | MacGregor . |
| 5,019,085 | 5/1991 | Hillstead . |
| 5,019,090 | 5/1991 | Pinchuk . |
| 5,035,706 | 7/1991 | Gianturco et al. . |
| 5,037,377 | 8/1991 | Alonso . |
| 5,037,427 | 8/1991 | Harada et al. . |
| 5,064,435 | 11/1991 | Porter . |
| 5,067,957 | 11/1991 | Jervis . |
| 5,092,877 | 3/1992 | Pinchuk . |
| 5,100,429 | 3/1992 | Sinofsky et al. . |
| 5,102,417 | 4/1992 | Palmaz . |
| 5,104,404 | 4/1992 | Wolff . |
| 5,122,154 | 6/1992 | Rhodes . |
| 5,123,917 | 6/1992 | Lee . |
| 5,133,732 | 7/1992 | Wiktor . |
| 5,139,480 | 8/1992 | Hickle et al. . |
| 5,147,370 | 9/1992 | McNamara et al. . |
| 5,151,105 | 9/1992 | Kwan-Gett . |
| 5,161,547 | 11/1992 | Tower . |
| 5,162,430 | 11/1992 | Rhee et al. . |
| 5,163,958 | 11/1992 | Pinchuk . |
| 5,171,262 | 12/1992 | MacGregor . |
| 5,192,307 | 3/1993 | Wall . |
| 5,195,984 | 3/1993 | Schatz . |
| 5,201,757 | 4/1993 | Heyn ........................................ 606/198 |
| 5,209,735 | 5/1993 | Lazarus . |
| 5,211,658 | 5/1993 | Clouse . |
| 5,213,580 | 5/1993 | Slepian et al. . |
| 5,217,483 | 6/1993 | Tower . |
| 5,221,261 | 6/1993 | Termin et al. . |
| 5,236,447 | 8/1993 | Kubo et al. . |
| 5,264,276 | 11/1993 | McGregor et al. . |
| 5,282,847 | 2/1994 | Trescony et al. . |
| 5,306,261 | 4/1994 | Alliger et al. . |
| 5,306,294 | 4/1994 | Winston ........................................ 623/1 |
| 5,324,304 | 6/1994 | Rasmussen ............................ 606/200 |
| 5,342,348 | 8/1994 | Kaplan . |
| 5,344,426 | 9/1994 | Lau et al. . |
| 5,356,423 | 10/1994 | Tihon et al. . |
| 5,360,443 | 11/1994 | Barone et al. . |
| 5,366,473 | 11/1994 | Winston et al. ........................ 606/198 |
| 5,372,600 | 12/1994 | Beyar et al. ............................ 606/108 |
| 5,382,261 | 1/1995 | Palmaz . |
| 5,405,378 | 4/1995 | Strecker . |
| 5,423,849 | 6/1995 | Eugelson et al. . |
| 5,443,500 | 8/1995 | Sigwart et al. ............................ 623/1 |
| 5,449,373 | 9/1995 | Pinchasik et al. . |
| 5,458,605 | 10/1995 | Klemm . |
| 5,480,423 | 1/1996 | Ravenscroft ................................ 623/1 |
| 5,484,444 | 1/1996 | Braunschweiler ..................... 606/108 |
| 5,496,365 | 3/1996 | Sgro . |
| 5,507,767 | 4/1996 | Maeda et al. ............................ 623/1 X |
| 5,509,902 | 4/1996 | Raulerson . |
| 5,522,881 | 6/1996 | Lentz . |
| 5,540,701 | 7/1996 | Sharkey et al. . |
| 5,540,712 | 7/1996 | Kleshinski et al. . |
| 5,545,210 | 8/1996 | Hess et al. . |
| 5,549,635 | 8/1996 | Solar . |
| 5,549,663 | 8/1996 | Cottone, Jr. . |
| 5,554,180 | 9/1996 | Turk . |
| 5,556,413 | 9/1996 | Lam . |
| 5,562,726 | 10/1996 | Chuter . |
| 5,571,173 | 11/1996 | Parodi . |
| 5,575,816 | 11/1996 | Rudnick et al. . |
| 5,591,197 | 1/1997 | Orth et al. . |
| 5,607,442 | 3/1997 | Fischell et al. . |
| 5,662,713 | 9/1997 | Andersen et al. . |

FOREIGN PATENT DOCUMENTS

| | | |
|---|---|---|
| WO 92/06734 | 4/1992 | WIPO . |
| WO 92/09246 | 6/1992 | WIPO . |
| WO 93/13825 | 7/1993 | WIPO . |
| WO 93/19803 | 10/1993 | WIPO . |
| WO 93/19804 | 10/1993 | WIPO . |
| WO 93/22986 | 11/1993 | WIPO . |
| WO 93/22989 | 11/1993 | WIPO . |
| WO 94/00179 | 1/1994 | WIPO . |
| WO 94/01483 | 1/1994 | WIPO . |
| WO 94/04097 | 3/1994 | WIPO . |
| WO 94/12136 | 6/1994 | WIPO . |
| WO 94/15549 | 7/1994 | WIPO . |
| WO 95/05132 | 2/1995 | WIPO . |

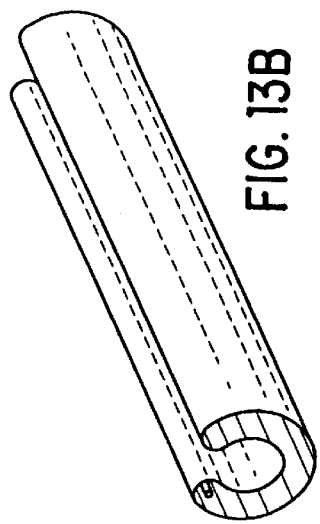
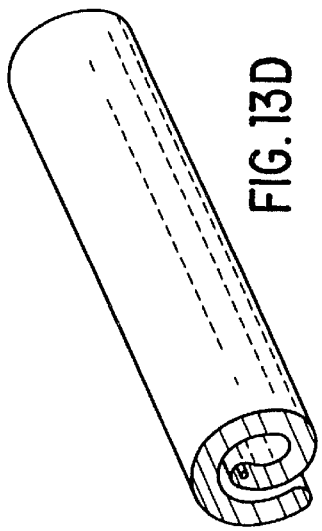
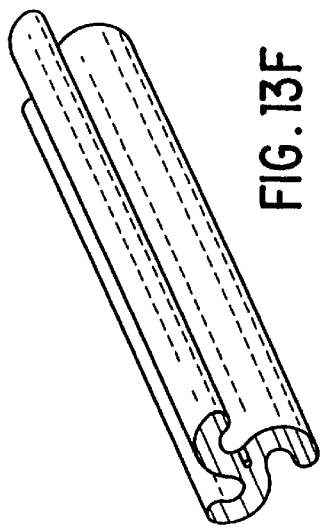
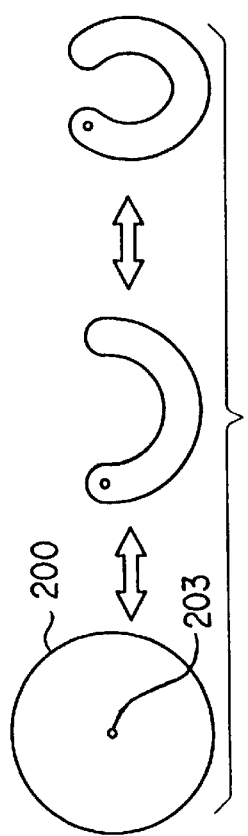
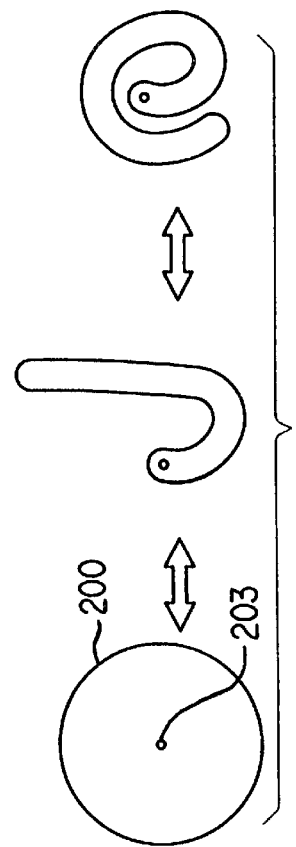
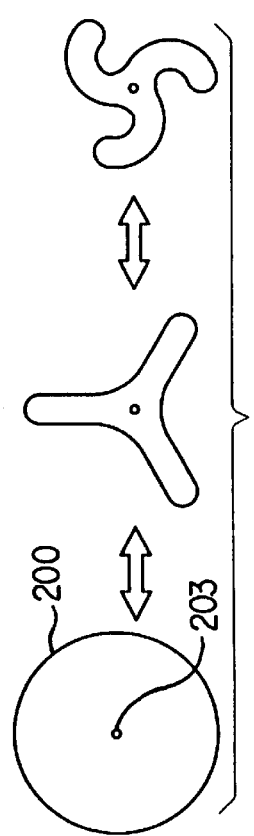

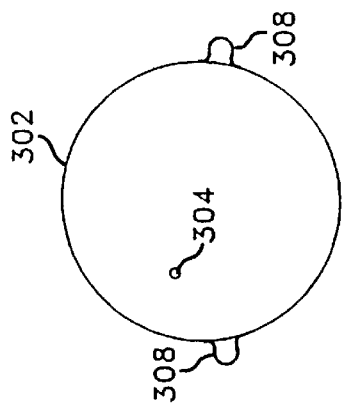
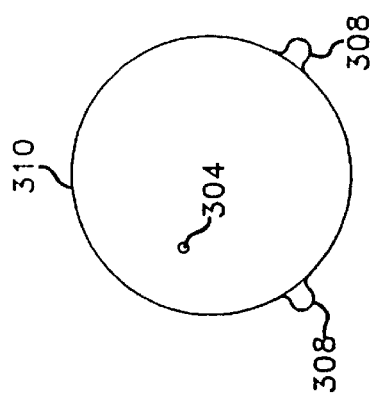
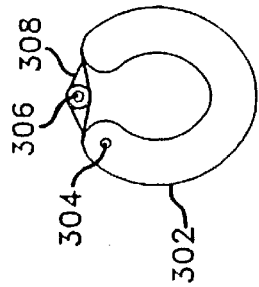
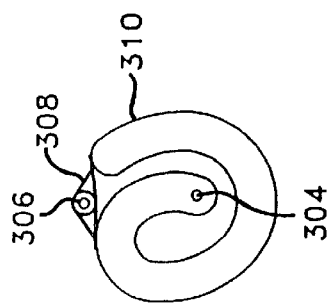
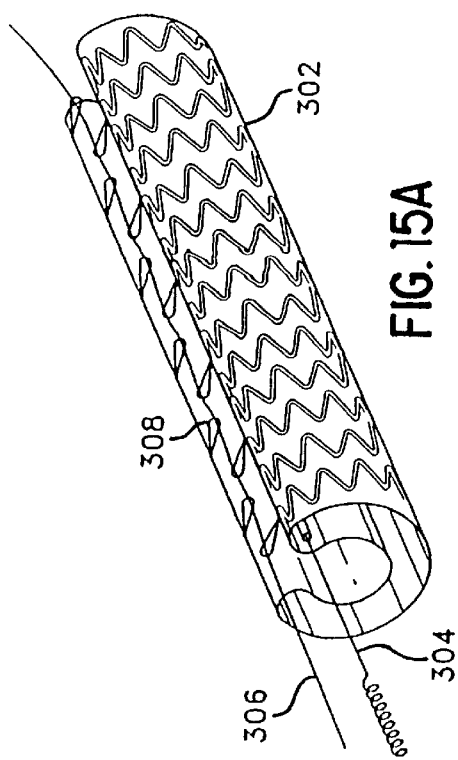
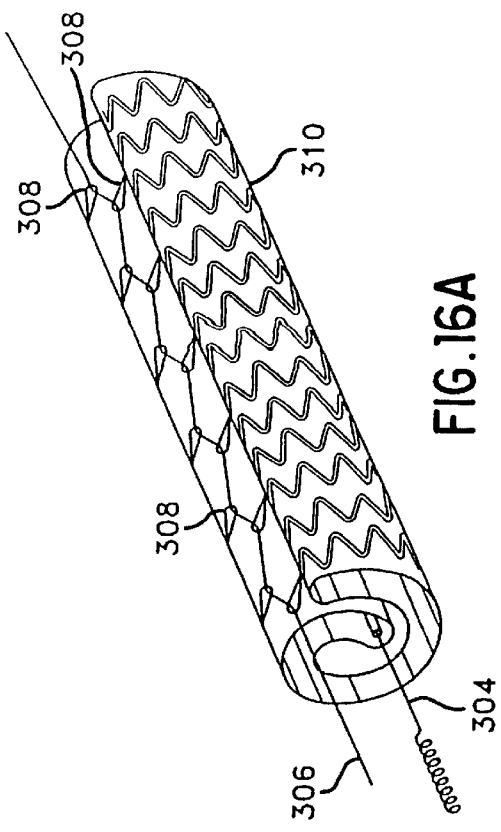

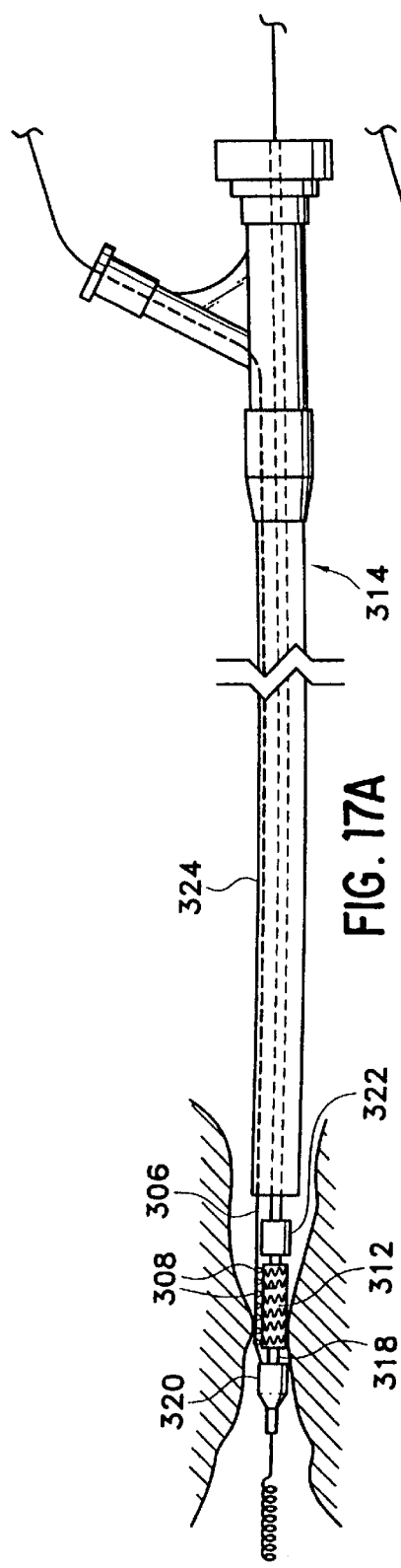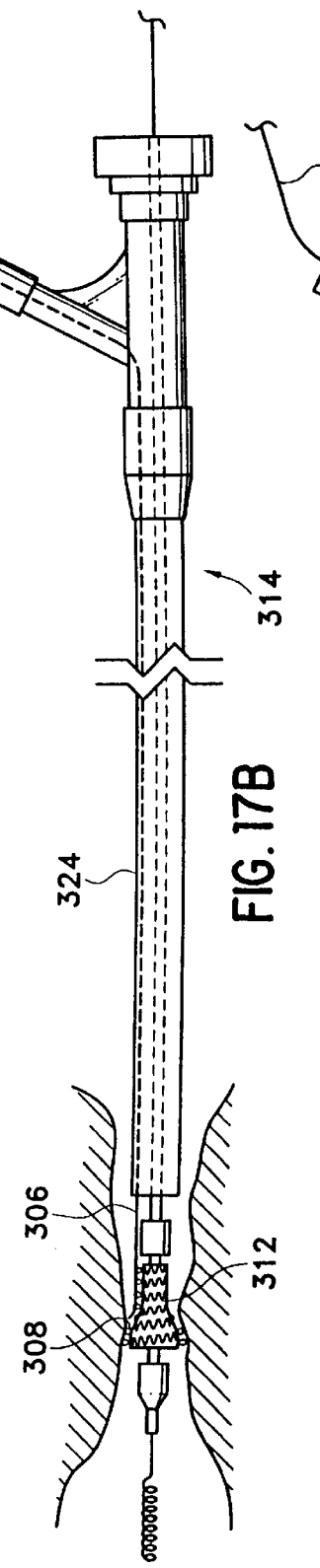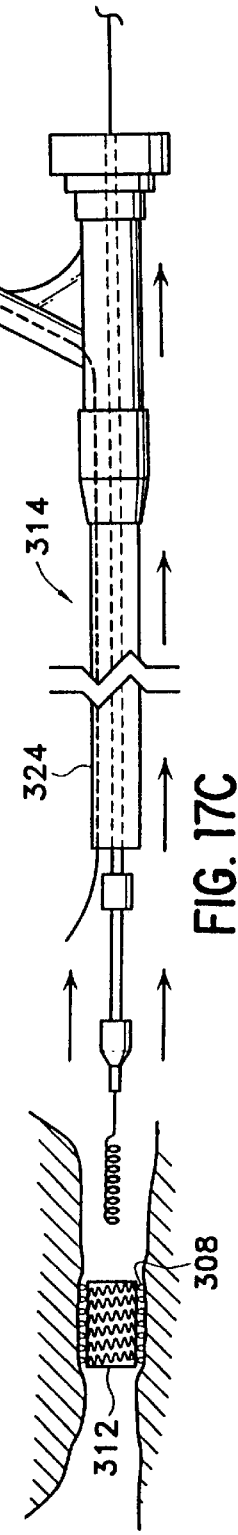

SELF-EXPANDABLE HELICAL INTRAVASCULAR STENT AND STENT-GRAFT

This application is a division of application Ser. No. 08/221,815 filed Apr. 1, 1994.

FIELD OF THE INVENTION

This invention is a medical device and a method of using it. The device is a foldable stent or stent-graft which may be percutaneously delivered with (or on) an endovascular catheter or via surgical techniques or using other suitable techniques and then expanded. The expandable stent structure utilizes at least one torsional member having an undulating shape which is helically deployed to form the generally cylindrical shape eventually deployed as the stent. The helical winding desirably is aligned to allow those undulating shapes in adjacent turns of the helix to be in phase. The adjacent undulating shapes maybe held in that phased relationship using a flexible linkage, often made of a polymeric material. The stent may be flared on at least one of its ends to promote smooth blood flow at that flare and to assure that the stent will remain in the chosen position within the body. The stent's configuration allows it to be folded or otherwise compressed to a very small diameter prior to deployment without changing the length of the stent. The stent may be expanded with the use of an installation device such as a balloon but preferably is used as a self-expandable device. The graft component cooperating With the stent is tubular and preferably is a blood-compatible collagenous material which may, if desired, be reinforced with fibers. The tubular graft member may be cast onto or otherwise attached or imbedded into the stent structure to form an integral stent-graft. Alternatively, the graft may be used to maintain the generally cylindrical shape of the stent, e.g., without the use of the flexible linkage.

The stent-graft may be used to reinforce vascular irregularities, to provide a smooth nonthrombogenic interior vascular surface for diseased areas in blood vessels, or to increase blood flow past a diseased area of a vessel by mechanically improving the interior surface of the vessel. The inventive stent-graft is especially suitable for use within smaller vessels between 2 mm and 6 mm in diameter but is equally suitable for significantly larger vessels. The invention provides a stent which is self-expanding, kink-resistant, easily bent along its longitudinal axis, does not change its length during that expansion, and is able to provide collapsible support for otherwise frangible graft material.

The invention involves procedures for deploying stents or stent-grafts which have been folded, bound, or otherwise collapsed to significantly smaller diameters for insertion into a human or animal body. When used with super-elastic alloys, the stent may be collapsed at a convenient temperature either above or, preferably, below the transition temperature of the alloy. The deployment procedures may involve the use of an outer sleeve to maintain the stent or stent-graft at a reduced diameter or may involve a "slip-line" or "tether wire" to hold and then to release the device.

BACKGROUND OF THE INVENTION

Treatment or isolation of vascular aneurysms or of vessel walls which have been thinned or thickened by disease has traditionally been done via surgical bypassing with vascular grafts. Shortcomings of this procedure include the morbidity and mortality associated with surgery, long recovery times after surgery, and the high incidence of repeat intervention needed due to limitations of the graft or of the procedure. Vessels thickened by disease are currently sometimes treated less invasively with intraluminal stents that mechanically hold these vessels open either subsequent to or as an adjunct to a balloon angioplasty procedure. Shortcomings of current stents include the use of highly thrombogenic materials (stainless steels, tantalum, ELGILOY) which are exposed to blood, the general failure of these materials to attract and support functional endothelium, the irregular stent/vessel surface that causes unnatural blood flow patterns, and the mismatch of compliance and flexibility between the vessel and the stent.

Important to this invention is the use of less invasive intraluminal delivery and, in a preferred aspect, placement of a nonthrombogenic blood-carrying conduit having a smooth inner lumen which will endothelize. The most preferred biologic material chosen for the inner layer of the inventive stent-graft is collagen-based and, although it will fold with ease, is otherwise fairly frangible or inelastic in that it has very little ability to stretch. Mounting a collagen tube on the outside of or as a part of a balloon-expandable stent will usually cause the tube to tear. Mounting such a tube on the inside of a balloon expandable stent will yield a torn irregular surface exposed to blood flow. Further, balloon expandable devices that rely upon plastic deformation of the stent to achieve a deployed shape are subject to abrupt closure as a result of trauma when the devices are placed in a vessel near the skin surface or across a joint or ligament. Those self-expanding stents which rely on the shortening of the stent upon radial expansion at deployment may cause vessel tearing problems similar to those observed with the use of balloon expandable devices. Obviously, stents which shorten during deployment are also subject to deployment placement inaccuracies.

The most desired variations of this invention involve a stent-graft which is self-expanding, which does not shorten upon delivery, which has excellent longitudinal flexibility, which has high radial compliance to the vessel lumen, exposes the blood to a smooth, nonthrombogenic surface capable of supporting endothelium growth.

The inventive device may be delivered in a reduced diameter and expanded to maintain the patency of any conduit or lumen in the body. An area in which the inventive stent and stent graft is particularly beneficial is in the scaffolding of atherosclerotic lesions in the cardiovascular system to establish vessel patency, prevention of thrombosis, and the further prevention of restenosis after angioplasty. In contrast to many of the stents discussed below having metallic struts intruding into the blood flow in the vessel lumen which generate turbulence and create blood stasis points initiating thrombus formation, the smooth, continuous surface provided by the preferred tubular collagen-based inner conduit of our invention provides a hemodynamically superior surface for blood flow.

The non-thrombogenic properties of the most preferred sPEG collagen surface results in a less thrombogenic device. Clinically, this allows a more moderate anti-coagulation regimen to be used. As a result, the rate of bleeding complications, a major drawback associated with stenting, may be reduced. The absence of gaps or holes in the graft structure between stent struts of our invention allows the tacking of both large and small flaps and tears in the vessel wall. These flaps disrupt blood flow and attract thrombus. The disruption of the natural anti-thrombotic covering of endothelium only worsens the condition. The collagen-based barrier we interpose between blood and a disrupted or injured portion of the vessel wall serves to mask injured intimal or medial layers from blood, thereby preventing thrombus formation and intimal proliferation which may lead to restenosis.

The presence of our inventive stent-graft acts as a mechanical barrier preventing tissue from proliferating into or impinging the lumen. The nature of the bioactivity of the collagen and the smoother flow characteristics at the blood-contacting surface are conducive to endothelial cell attachment and growth thereby assuring the long-term blood compatibility of the device.

Mechanically, our inventive linked helical stent structure provides a good combination of radial strength and flexibility. The structure is also radially resilient. It can be completely crushed or flattened and yet spring open again once the obstructive loading is removed. This ability is important for use in exposed portions of the body around the peripheral vasculature or around joints. The stent-graft can sustain a crushing traumatic blow or compression from the bending of a joint and still return to the open configuration once the load is removed.

With regard to delivery, the self-expansion mechanism eliminates the need for a balloon catheter and the associated balloon rupture problems often associated with balloons. In addition, the absence of the bulk of the balloon allows a smaller delivery profile to be achieved. Unlike some other self-expanding stent designs, this stent-graft maintains a constant length throughout the expansion process. Thus, the stent-graft would not have some of the positioning problems associated with other many self-expanding stents. In treating longer lesions, our self-expanding design eliminates the need for special long balloons or repositioning of the balloon between inflations in order to expand the entire length of the stent.

When used as a conventional vascular graft or intraluminal graft, our most preferred stent-grafts offer a number of advantages over existing technologies. Unlike expanded polytetrafluoroethylene (PTFE) grafts, the collagen-based material supports endothelial cell growth and is incorporated into the surrounding tissue. As an intraluminal graft, the device has several advantages. The wall thickness may be made thinner than either of current stents and expanded PTFE or of tanned, reinforced biologic grafts. When placed inside the lumen of a vessel, a thin-walled graft results in a larger opening for blood flow resulting in improved hemodynamics. Lastly, when used as an intraluminal graft, there is no anastomosis site. Anastomosis sites are thought to be a common source of problems associated with graft failures.

The impermeability of the preferred stent-graft makes it suitable for shunting and thereby hydraulically isolating aneurysms. The expansile properties derived from the stent structure provide a secure anchor to the vessel wall. The stent reinforces the collagen-based tubular component, much as a fiber tube would, increasing the burst strength of the stent-graft.

Finally, the organic composition of the preferred collagen-based materials used in the inventive stent-graft provides an excellent vehicle for localized drug delivery, certainly better than metallic stents or other synthetic grafts. In addition, therapeutic compounds may be linked, conjugated, or otherwise more easily bound to the organic graft material (or to its substituents, such as PEG) than to the surface of a metallic structure. Localized drug delivery is desirable in preventing thrombosis or restenosis. Therapeutically effective doses may be administered to the target area without systemic concentrations being raised. This capability is of great benefit in reducing side-effects and complications associated with drug therapy.

Therapeutic agents may be delivered out of the collagen matrix by diffusion. Alternatively, these agents may be bound temporarily or permanently on the collagen surfaces. Different agents may be bound on the inner and outer surfaces to achieve different therapeutic ends. For example, a drug to minimize thrombus formation might be appropriate for the inside, blood-contacting surface, while a drug which would inhibit smooth muscle cell proliferation might be appropriate on the outer surface. Drugs can be chemically or physically bound to either the sPEG or the collagen molecules.

Stents

The stents currently described in the open literature include a wide variety of different shapes.

Wallsten, U.S. Pat. No. 4,655,771, suggests a vascular prosthesis for transluminal implantation which is made up of a flexible tubular body having a diameter that is varied by adjusting the axial separation of the two ends of the body relative to each other. In general, the body appears to be a woven device produced of various plastics or stainless steel.

U.S. Pat. No. 4,760,849, to Kroph, shows the use of a ladder-shaped coil spring which additionally may be used as a filter in certain situations.

Porter, U.S. Pat. No. 5,064,435, suggests a stent made up of two or more tubular stent segments which may be deployed together so to produce a single axial length by a provision of overlapping areas. This concept is to permit the use of segments of known length, which, when deployed, may be used together in overlapping fashion additively to provide a stent of significant length.

Quan-Gett, U.S. Pat. No. 5,151,105, discloses an implantable, collapsible tubular sleeve apparently of an outer band and an inner spring used to maintain the sleeve in a deployed condition.

Wall, U.S. Pat. No. 5,192,307, suggests a stent having a number of holes therein and which is expandable using an angioplasty balloon so to allow ratchet devices or ledges to hold the stent in an open position once it is deployed.

Perhaps of more relevance are the patents using wire as the stent material.

Gianturco, in U.S. Pat. Nos. 4,580,568 and 5,035,706, describes stents formed of stainless steel wire arranged in a closed zigzag pattern. The stents are compressible to a reduced diameter for insertion into and removal from a body passageway. The stents appear to be introduced into the selected sites by discharge of the collapsed zigzag wire configuration from the tip of a catheter.

U.S. Pat. Nos. 4,830,003 and 5,104,404, to Wolff et al., shows a stent of a zigzag wire configuration very similar in overall impression to the Gianturco device. However, the stent is said to be self-expanding and therefore does not need the angioplasty balloon for its expansion.

Hillstead, U.S. Pat. No. 4,856,516, suggests a stent for reinforcing vessel walls made from a single elongated wire. The stent produced is cylindrical and is made up of a series of rings which are, in turn, linked together by half-hitch junctions produced from the single elongated wire. It is not helically wound, nor is there a second linking member tending to link the helices together.

Wiktor, U.S. Pat. Nos. 4,649,992, 4,886,062, 4,969,458, and 5,133,732, shows wire stent designs using variously a zigzag design or, in the case of Wiktor '458, a helix which winds back upon itself. Wiktor '062 suggests use of a wire component made of a low-memory metal such as copper, titanium or gold. These stents are to be implanted using a balloon and expanded radially for plastic deformation of the metal.

Wiktor '458 is similarly made of low-memory alloy and is to be plastically deformed upon its expansion on an angioplasty balloon.

Wiktor '732 teaches the use of a longitudinal wire welded to each turn of the helically wound zig-zag wire which is said to prevent the longitudinal expansion of the stent during deployment. A further variation of the described stent includes a hook in each turn of the helix which loops over a turn in an adjacent turn. Neither variation includes a flexible linkage between adjacent helices.

WO93/13825, to Maeda et al, shows a self-expanding stent similar to the Gianturco, Wolff, and Wiktor designs, formed of stainless steel wire, which is built into an elongated zig-zag pattern, and helically wound about a central axis to form a tubular shape interconnected with a filament. The bends of the helix each have small loops or "eyes" at their apexes which are inter-connected with a filament. Because of the teaching to connect the eyes of the apexes, the stent appears to be a design that axially expands during compression and may tear attached grafts because of the relative change in position of the arms of the zig-zag during compression of the stent.

MacGregor, U.S. Pat. No. 5,015,253, shows a tubular non-woven stent made up of a pair of helical members which appear to be wound using opposite "handedness". The stent helices desirably are joined or secured at the various points where they cross.

Pinchuk, in U.S. Pat. Nos. 5,019,090, 5,092,877, and 5,163,958, suggests a spring stent which appears to circumferentially and helically wind about as it is finally deployed except, perhaps, at the very end link of the stent. The Pinchuk '958 patent further suggests the use of a pyrolytic carbon layer on the surface of the stent to present a porous surface of improved antithrombogenic properties. The helices are not linked to each other, however, nor is there any suggestion that the helices be maintained in a specific relationship either as deployed or as kept in the catheter prior to deployment.

U.S. Pat. No. 5,123,917, to Lee, suggests an expandable vascular graft having a flexible cylindrical inner tubing and a number of "scaffold members" which are expandable, ring-like, and provide circumferential rigidity to the graft. The scaffold members are deployed by deforming them beyond their plastic limit using, e.g., an angioplasty balloon.

Tower, in U.S. Pat. Nos. 5,161,547 and 5,217,483, shows a stent formed from a zig-zag wire wound around a mandrel in a cylindrical fashion. It is said to be made from "a soft platinum wire which has been fully annealed to remove as much spring memory as possible." A longitudinal wire is welded along the helically wound sections much in the same way as was the device of Wiktor.

There are a variety of disclosures in which super-elastic alloys such as nitinol are used in stents. See, U.S. Pat. No. 4,503,569, to Dotter; U.S. Pat. No. 4,512,338, to Balko et al.; U.S. Pat. No. 4,990,155, to Wilkoff; U.S. Pat. No. 5,037,427, to Harada, et al.; U.S. Pat. No. 5,147,370, to MacNamara et al.; U.S. Pat. No. 5,211,658, to Clouse; and U.S. Pat. No. 5,221,261, to Termin et al. None of these references suggest a device having discrete, individual, energy-storing torsional members as are required by this invention.

Jervis, in U.S. Pat. Nos. 4,665,906 and 5,067,957, describes the use of shape memory alloys having stress-induced martensite properties in medical devices which are implantable or, at least, introduced into the human body.

Stent-Grafts

A variety of stent-graft designs are shown in the following literature.

Perhaps the most widely known such device is shown in Ersek, U.S. Pat. No. 3,657,744. Ersek shows a system for deploying expandable, plastically deformable stents of metal mesh having an attached graft through the use of an expansion tool.

Palmaz describes a variety of expandable intraluminal vascular grafts in a sequence of patents: U.S. Pat. Nos. 4,733,665; 4,739,762; 4,776,337; and 5,102,417. The Palmaz '665 patent suggests grafts (which also function as stents) that are expanded using angioplasty balloons. The grafts are variously a wire mesh tube or of a plurality of thin bars fixedly secured to each other. The devices are installed, e.g., using an angioplasty balloon and consequently are not seen to be self-expanding.

The Palmaz '762 and '337 patents appear to suggest the use of thin-walled, biologically inert materials on the outer periphery of the earlier-described stents.

Finally, the Palmaz '417 patent describes the use of multiple stent sections each flexibly connected to its neighbor.

Rhodes, U.S. Pat. No. 5,122,154, shows an expandable stent-graft made to be expanded using a balloon catheter. The stent is a sequence of ring-like members formed of links spaced apart along the graft. The graft is a sleeve of a material such as expanded a polyfluorocarbon, e.g., GORE-TEX or IMPRAGRAFT.

Schatz, U.S. Pat. No. 5,195,984, shows an expandable intraluminal stent and graft related in concept to the Palmaz patents discussed above. Schatz discusses, in addition, the use of flexibly-connecting vascular grafts which contain several of the Palmaz stent rings to allow flexibility of the overall structure in following curving body lumen.

Cragg, "Percutaneous Femoropopliteal Graft Placement", *Radiology*, vol. 187, no. 3, pp. 643–648 (1993), shows a stent-graft of a self-expanding, nitinol, zig-zag, helically wound stent having a section of polytetrafluoroethylene tubing sewed to the interior of the stent.

Cragg (European Patent Application 0,556,850) discloses an intraluminal stent made up of a continuous helix of zig-zag wire and having loops at each apex of the zig-zags. Those loops on the adjacent apexes are individually tied together to form diamond-shaped openings among the wires. The stent may be made of a metal such as nitinol (col. 3, lines 15–25 and col. 4, lines 42+) and may be associated with a "polytetrafluoroethylene (PTFE), dacron, or any other suitable biocompatible material". Those biocompatible materials may be inside the stent (col. 3, lines 52+) or outside the stent (col. 4, lines 6+). There is no suggestion that the zig-zag wire helix be re-aligned to be "in phase" rather than tied in an apex-to-apex alignment. The alignment of the wire and the way in which it is tied mandates that it expand in length as it is expanded from its compressed form.

Grafts

As was noted above, the use of grafts in alleviating a variety of vascular conditions is well known. Included in such known grafting designs and procedures are the following.

Medell, U.S. Pat. No. 3,479,670, discloses a tubular prothesis adapted to be placed permanently in the human body. It is made of framework or support of a synthetic fiber such as DACRON or TEFLON. The tube is said to be made more resistant to collapse by fusing a helix of a polypropylene monofilament to its exterior. The reinforced fabric tube is then coated with a layer of collagen or gelatin to render the tubing (to be used as an esophageal graft) impermeable to bacteria or fluids.

Sparks, in U.S. Pat. Nos. 3,514,791, 3,625,198, 3,710,777, 3,866,247, and 3,866,609, teach procedures for the production of various graft structures using dies of suitable shape and a cloth reinforcing material within the die. The die and reinforcement are used to grow a graft structure using a patient's own tissues. The die is implanted within the human body for a period of time to allow the graft to be produced. The graft is in harvested and implanted in another site in the patient's body by a second surgical procedure.

Braun, in U.S. Pat. No. 3,562,820, shows a biological prosthesis manufactured by applying onto a support of a biological tissue (such as serosa taken from cattle intestine) a collagen fiber paste. The procedure is repeated using multiple layers of biological tissue and collagen fiber paste until a multi-layer structure of the desired wall thicknesses is produced. The prosthesis is then dried and removed prior to use.

Dardik et al, U.S. Pat. No. 3,974,526, shows a procedure for producing tubular prostheses for use in vascular reconstructive surgeries. The prosthesis is made from the umbilical cord of a newly born infant. It is washed with a solution of 1 percent hydrogen peroxide and rinsed with Ringer's lactate solution. It is then immersed in a hyaluronidase solution to dissolve the hyaluronic acid coating found in the umbilical cord. The vessels are then separated from the cord and their natural interior valving removed by use of a tapered mandrel. The vessels are then tanned with glutaraldehyde. A polyester mesh support is applied to the graft for added support and strength.

Whalen, U.S. Pat. No. 4,130,904, shows a prosthetic blood conduit having two concentrically associated tubes with a helical spring between them. Curved sections in the tube walls help prevent kinking of the tube.

Ketharanathan, U.S. Pat. No. 4,319,363, shows a procedure for producing a vascular prosthesis suitable for use as a surgical graft. The prosthesis is produced by implanting a rod or tube in a living host and allowing collagenous tissue to grow on the rod or tube in the form of coherent tubular wall. The collagenous implant is removed from the rod or tube and tanned in glutaraldehyde. The prosthesis is then ready for use.

Bell, U.S. Pat. No. 4,546,500, teaches a method for making a vessel prosthesis by incorporating a contractile agent such as smooth muscle cells or platelets into a collagen lattice and contracting the lattice around a inner core. After the structure has set, additional layers are applied in a similar fashion. A plastic mesh sleeve is desirably sandwiched between the layers or imbedded within the structure to provide some measure of elasticity.

Hoffman Jr. et al, U.S. Pat. No. 4,842,575, shows a collagen impregnated synthetic vascular graft. It is made of a synthetic graft substrate and a cross-linked collagen fibril. It is formed by depositing a aqueous slurry of collagen fibrils into the lumen of the graft and massaging the slurry into the pore structure of the substrate to assure intimate admixture in the interior. Repeated applications and massaging and drying is said further to reduce the porosity of the graft.

Alonoso, U.S. Pat. No. 5,037,377, is similar in overall content to the Hoffman Jr. et al patent discussed above except that, in addition to collagen fibers, soluble collagen is introduced into the fabric. A suitable cross-linking agent such as glutaraldehyde is used to bond adjacent collagen fibers to each other.

Slepian et al, U.S. Pat. No. 5,213,580, teaches a process described as "paving" or "stabilizing by sealing the interior surface of a body vessel or organ" by applying a biodegradable polymer such as a polycaprolactone. The polymer is made into a tubular substrate, placed in position, and patched into place.

Finally, there are known vascular grafts using collagenous tissue with reinforcing structure. For instance, Pinchuk, in U.S. Pat. Nos. 4,629,458 and 4,798,606, suggests the use of collagen with some other type of fibrous structure supporting the collagen as a biograft. Similarly, Sinofsky et al., U.S. Pat. No. 5,100,429, suggests a partially-cured, collagen-based material used to form a graft within a blood vessel.

Kreamer, U.S. Pat. No. 4,740,207, suggests a intraluminal graft made of a semi-rigid resilient tube, open along a seam extending from one end to the other, which is expanded within the vessel and which resulting larger diameter is maintained by use of a ledge at the longitudinal seam for catching the opposite side of the seam on the expanded graft.

We have found that elasticity, or the ability of a material to return to its original shape after a deformation, can be maintained in smaller stents by the distribution of folding deformation throughout the structure. By incorporating hinges or hinge regions into the structure, the distribution of "local" folding deformation is maximized. The hinge regions include torsion members allowing a significant portion of the folding displacement to be re-oriented parallel to the longitudinal axis of the stent-graft. The act of folding, crushing, or otherwise elastically deforming the stent creates a significant torsional component in the torsion members which component is parallel to that longitudinal axis. The hinges are positioned at least at each of the fold points around the circumference of the stent where folding is desired. The circumferentially oriented regions of the stents, which connect the torsion members, pivot about the torsion members, causing the torsion members to undergo a twisting deformation. In order to avoid exceeding the elastic limit of the material, the length of the torsion members is increased to lower the amount of twist per length or strain imposed. The orientation of the torsion members is such that their length does not increase the circumference of the device. None of the cited references suggest such a device.

SUMMARY OF THE INVENTION

This invention is a foldable stent or stent-graft which may be percutaneously delivered through or over an endovascular catheter or using surgical techniques or other appropriate methodologies. The expandable stent structure utilizes torsional regions which allow it to be folded to a very small diameter prior to deployment. The torsional members have an undulating shape which may be helically deployed to form the stent's cylindrical shape. The undulating shape may be aligned to allow the shapes in adjacent turns of the helix to be in phase. The undulating shapes may be generally V-shaped, U-shaped, sinusoidal, or ovoid. Adjacent undulating shapes may be held in the phased relationship using a flexible linkage, often made of a polymeric material. The undulating torsional members do not have any means at (or near) the apex of the undulating shapes which would tend to constrict the movement of the flexible linkage during compression of the stent. The stent may be expanded with the use of an installation device such as an angioplasty balloon but preferably is used as a self-expandable device. The graft component used to complement the stent is tubular and preferably is of a collagenous material which may, if desired, be reinforced with fibers of random, woven, roving, or wound configurations. The tubular member preferably is cast onto or otherwise attached or imbedded into the stent structure. The stent-graft may be used to reinforce vascular irregularities and provide a smooth interior vascular surface, particularly within smaller vessels.

BRIEF DESCRIPTION OF THE DRAWINGS

FIGS. 13A, 13C, and 13E show procedures for folding the stent-grafts made according to the invention. FIGS. 13B, 13D, and 13F show the corresponding folded stent-grafts.

FIGS. 15A and 16A show front quarter views of folded stents or stent-grafts held in that folded position by a tether wire. FIGS. 15B, 15C, 16B, and 16C show end views of the folded stent and of the open stent shown respectively in FIGS. 15A and 16A.

FIGS. 17A–17C show a schematic procedure for deploying the inventive stent-grafts (as shown in FIGS. 15A–15C and 16A–16C) using a tether wire.

DESCRIPTION OF THE INVENTION

Figure 1A:
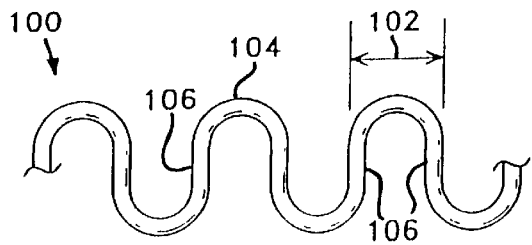
FIGS. 1A, 1B, 1C, 1D, and 1E are plan views of an unrolled stent form making up the invention.

As was noted above, this invention is variously an expandable stent, a stent-graft, and a fiber reinforced stent-graft. The stent-graft may be a combination of several components: a thin-walled tube generally coaxial with the stent, the expandable stent structure, and an optional network of fibers used to reinforce the tubular component. The stent and the optional reinforcing fibers are desirably imbedded in the wall of the thin-walled tube. The expandable stent structure is a cylindrical body produced of a helically placed (wound or otherwise preformed) torsion member having an undulating or serpentine shape. When the undulating torsion member is formed into the cylinder, the undulations may be aligned so that they are "in phase" with each other. The undulations are desirably linked, typically with a flexible linkage of a suitable polymeric material, to maintain the phased relationship of the undulations during compression and deployment. These stent configurations are exceptionally kink-resistant and flexible, particularly when flexed along the longitudinal axis of the stent.

When the stent is used in a reinforced stent-graft, that is to say: the stent is included into a thin-walled tube having reinforcing fibers, the fibers may be formed into a network, such as a tubular mesh. The stent-graft may be delivered percutaneously through the vasculature after having been folded to a reduced diameter. Once reaching the intended delivery site, it is expanded to form a lining on the vessel wall.

Methods of delivering the various devices using a percutaneous catheter either with or without expansion aids are also an aspect of the invention.

Stent Component

The materials typically used for vascular grafts, e.g., collagen, usually do not have the stiffness or strength by themselves both to stay open against the radial inward loads found in those vessels and to prevent their slippage from the chosen deployment site. In order to provide the strength required, a radially rigid stent structure may be incorporated into the stent-graft. Our stent is constructed of a reasonably high strength material, i.e., one which is resistant to plastic deformation when stressed. The structure is typically from one of three sources: 1.) a wire form in which a wire is first formed into an undulating shape and the resulting undulating shape is helically wound to form a cylinder, 2.) an appropriate shape is formed from a flat stock and wound into a cylinder, and 3.) a length of tubing is formed into an appropriate shape. These stent structures are typically oriented coaxially with the tubular graft component. The stent structures may be placed on the outer surface or the inner surface of the tubular member although it is preferable that the stent be imbedded in the graft tubing wall for ease of integration with the tubing and to prevent the stent's exposure to blood. It is desired that the stent structure have the strength and flexibility to tack the graft tubing firmly and conformally against the vessel wall. In order to minimize the wall thickness of the stent-graft, the stent material should have a high strength-to-volume ratio. Use of designs according to this invention provides stents which are shorter in length than those often used in the prior art. Additionally, the designs do not suffer from a tendency to twist (or helically unwind) or to shorten as the stent is deployed. As will be discussed below, materials suitable in these stents and meeting these criteria include various metals and some polymers.

A percutaneously delivered stent-graft must expand from a reduced diameter, necessary for delivery, to a larger deployed diameter. The diameters of these devices obviously vary with the size of the body lumen into which they are placed. For instance, the stents of this invention may range in size (for neurological applications) from 2.0 mm in diameter to 30 mm in diameter (for placement in the aorta). A range of about 2.0 mm to 6.5 mm (perhaps to 10.0 mm) is believed to be desirable. Typically, expansion ratios of 2:1 or more are required. These stents are capable of expansion ratios of up to 5:1 for larger diameter stents. Typical expansion ratios for use with the stents and stent-grafts of the invention typically are in the range of about 2:1 to about 4:1 although the invention is not so limited. The thickness of the stent materials obviously varies with the size (or diameter) of the stent and the ultimate required yield strength of the folded stent. These values are further dependent upon the selected materials of construction. Wire used in these variations are typically of stronger alloys, e.g., nitinol and stronger spring stainless steels, and have diameters of about 0.002 inches to 0.005 inches. For the larger stents, the appropriate diameter for the stent wire may be somewhat larger, e.g., 0.005 to 0.020 inches. For flat stock metallic stents, thicknesses of about 0.002 inches to 0.005 inches is usually sufficient. For the larger stents, the appropriate thickness for the stent flat stock may be somewhat thicker, e.g., 0.005 to 0.020 inches.

The stent-graft is fabricated in the expanded configuration. In order to reduce its diameter for delivery the stent-graft would be folded along its length, similar to the way in which a PCTA balloon would be folded. It is desirable, when using super-elastic alloys which are also have temperature-memory characteristics, to reduce the diameter of the stent at a temperature below the transition-temperature of the alloys. Often the phase of the alloy at the lower temperature is somewhat more workable and easily formed. The temperature of deployment is desirably above the transition temperature to allow use of the super-elastic properties of the alloy.

As a generic explanation of the mechanical theory of the inventive stent, reference is made to FIGS. 1A, 1B, 1C, 1D, 1E, 2, 3, and 4. FIG. 1A is a plan view of an isolated section of the inventive stent device and is intended both to identify a variation of the invention and to provide conventions for naming the components of the torsion member (100). FIG. 1A shows, in plan view, an undulating torsion member (100) formed from a wire stock into a U-shape. A torsion pair (102) is made up of an end member (104) and two adjacent torsion lengths (106). Typically, then, each torsion length (106) will be a component to each of its adjacent torsion pairs (102). The U-shaped torsion pair (102) may be characterized by the fact that the adjacent torsion lengths are generally parallel to each other prior to formation into the stent.

Generically speaking, the stents of this invention use undulating torsion members which are "open" or "unconfined" at their apex or end member (104). By "open" or "unconfined" we mean that the apex or end member (104) does not have any means in that apex which would tend to inhibit the movement of the flexible linkage (discussed below) down between the arms or torsion lengths (106) of the torsion pair (102).

Figure 1B:
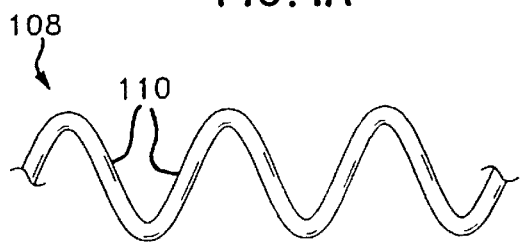

FIG. 1B shows another variation of the invention having a sinusoidal shaped torsion member (108). In this variation, the adjacent torsion lengths (110) are not parallel and the wire forms an approximate sine shape before being formed into a cylinder.

Figure 1C:
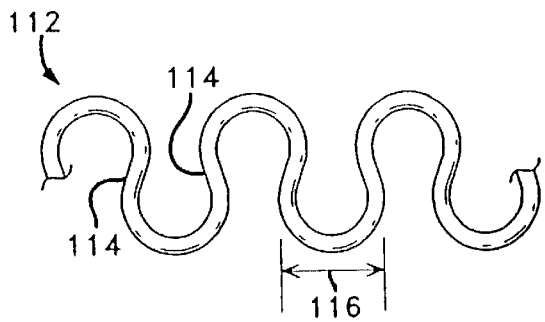

FIG. 1C shows a variation of the invention having an ovoid shaped torsion member (112). In this variation, the adjacent torsion lengths (114) are again not parallel. The wire forms an approximate open-ended oval with each torsion pair (116) before being formed into a cylinder.

Figure 1D:
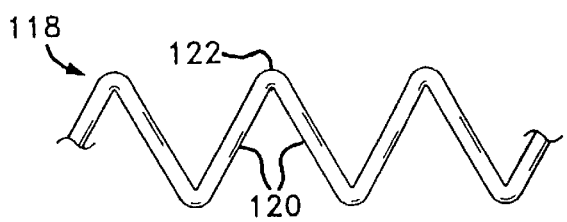

FIG. 1D shows another variation of the invention having a V-shaped torsion member (118). In this variation, the adjacent torsion lengths (120) form a relatively sharp angle at the torsion end (122) shape before being formed into a cylinder.

Figure 1E:
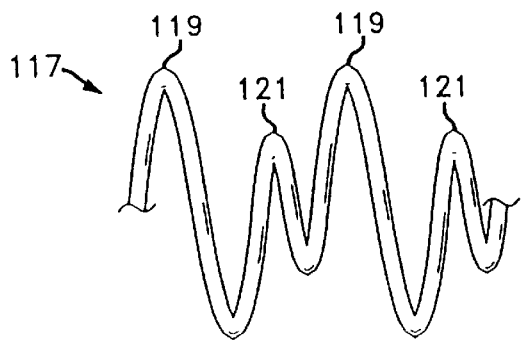

FIG. 1E shows a variation of the invention in which adjacent torsion members on the stent (117) have differing amplitude. The peaks of the high amplitude torsion members (119) may be lined up "out of phase" or "peak to peak" with short amplitude (121) or high amplitude torsion members in the adjacent turn of the helix or may be positioned "in phase" similar to those discussed with regard to FIG. 2 below.

The configurations shown in FIGS. 1A–1E are exceptionally kink-resistant and flexible when flexed along the longitudinal axis of the stent.

As ultimately deployed, a section of the torsion member found on one of FIGS. 1A–1D would be helically wound about a form of an appropriate size so that the end members (e.g., 104 in FIG. 1A) would be centered between the end members of the torsion member on an adjacent turn of the helix. This is said to be "in phase". "Out of phase" would be the instance in which the adjacent members meet directly, i.e., end member-to-end member. In any event, once so aligned, the phasic relationship may be stabilized by weaving a flexible linkage through the end members from one turn of the helix to the next.

Figure 2:
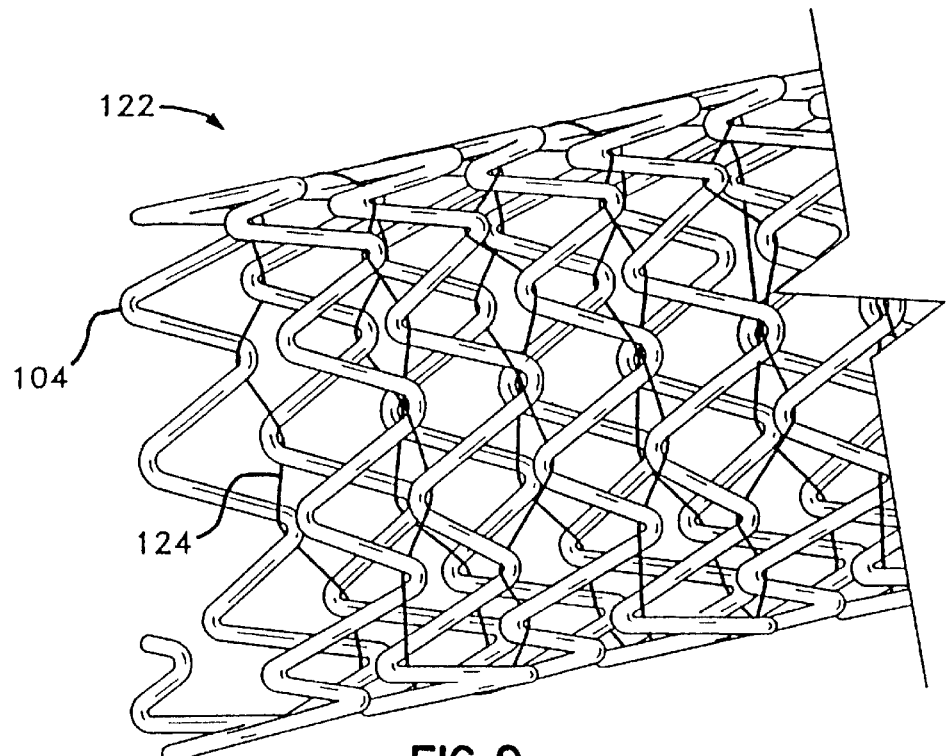
FIG. 2 is a side view of the inventive stent.
Figure 3:
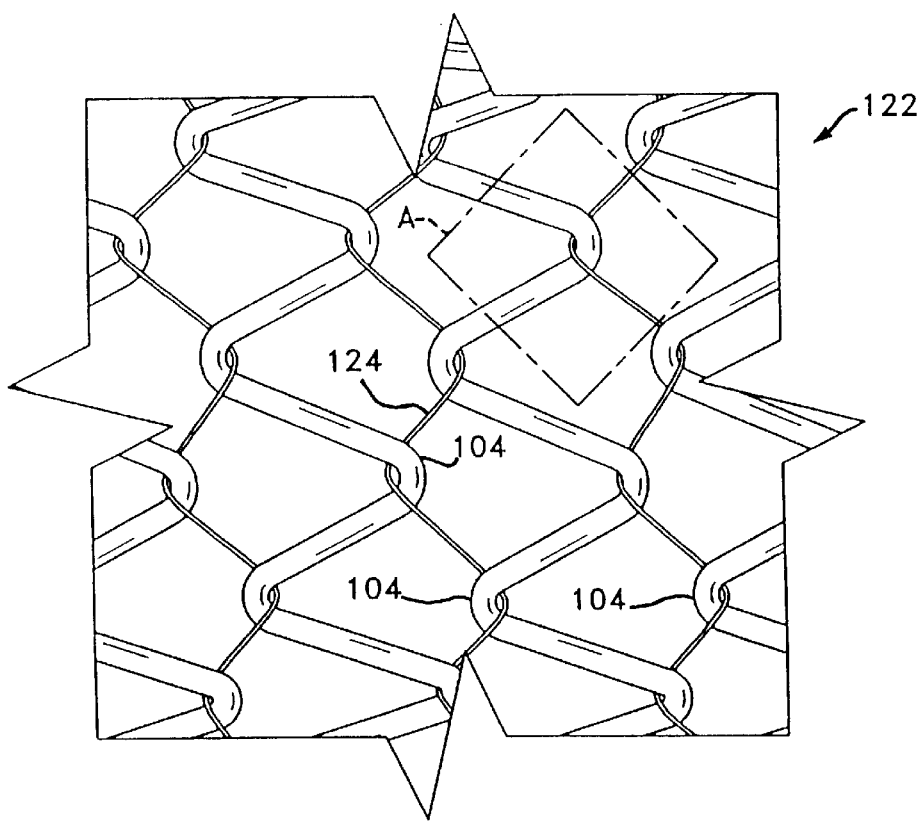
FIG. 3 is a close-up of a portion of the inventive stent shown in FIG. 2.

FIG. 2 shows a side view of a typical stent (122) made according to this invention including the phased relationship of the helical turns of the stent and the flexible linkage (124). FIG. 3 shows a close-up of the FIG. 2 stent and depicts the phased relationship (within box A) and shows in detail a typical way in which the flexible linkage (124) is looped through the various end members (104) to maintain the phased relationship as shown in FIG. 3, undulations in adjacent helical turns may be maintained in-phase with the flexible linkage (124). It may be noted that the flexible linkage (124) is free to move away from the apex at the end members (104) without constraint.

Figure 4:
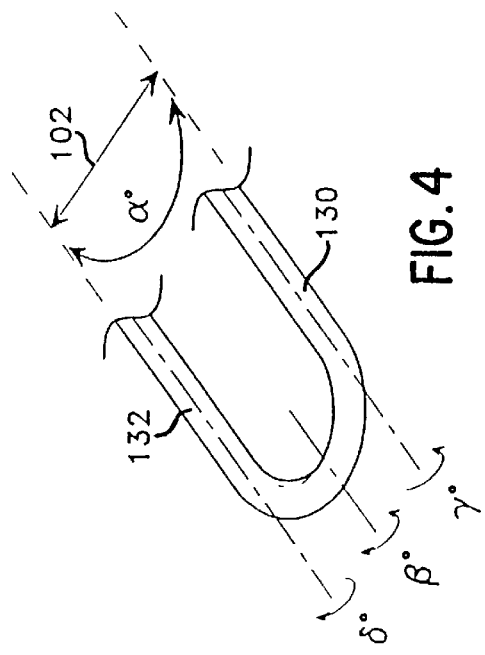
FIG. 4 is an abstracted portion of an inventive stent and shows the concept of torsion on a portion of the stent.

The stent may be folded in some fashion (as will be discussed below) for deployment. During the step of folding, the stent undergoes a transformation. FIG. 4 shows an isolated torsion pair (102). When the torsion pair (102) undergoes a flexing in the amount of $\alpha°$, the end member will flex some amount $\beta°$, torsion length (130) will undertake a twist of $\gamma°$, and torsion length (132) will undertake a twist opposite of that found in torsion length (130) in the amount of $\delta°$. The amounts of angular torsion found in the torsion lengths (130 and 132) will not necessarily be equal because the torsion lengths are not necessarily at the same angle to the longitudinal axis of the stent. Nevertheless, the sum of $\beta°+\gamma°+\delta°$ will equal $\alpha°$. When a value of $\alpha°$ is chosen, as by selection of the shape and size of the stent upon folding, the values of the other three angles ($\beta°,\gamma°,\delta°$) are chosen by virtue of selection of number of torsion pairs around the stent, size and physical characteristics of the wire, and length of the torsion lengths (103 and 132). Each of the noted angles must not be so large as to exceed the values at which the chosen material of construction plastically deforms at the chosen value of $\alpha°$.

To further explain the invention: it should understood that the torsion pair (102) undergoes a significant of flexing as the stent is folded or compressed in some fashion. The flexing provides a twist to the torsion lengths (103 and 132), a significant portion of which is generally parallel to the longitudinal axis of the stent. It is this significant imposed longitudinal torsion which forms an important concept of the inventive stent.

As noted elsewhere, in one very desirable variation of the inventive stent, as deployed in FIGS. 2 and 3, the stent is folded longitudinally and is delivered through the lumen of the catheter in such a way that it is self-restoring once it has been introduced to the selected body lumen site. This stated desire is not to rule out the use of the inventive stent or stent-graft with a balloon or expander or other shape-restoring tool if so desired, but the design of the stent is meant to eliminate the need for (or, at least to minimize the need for) such expanding tools.

With that preliminary background in place, it should be apparent that a simple tube of metal will undergo plastic deformation when sufficient force is applied radially to the outside of the tube. The amount of force needed to cause that plastic deformation will depend on a wide variety of factors, e.g., the type of metal utilized in the tube, the width of the tube, the circumference of the tube, the thickness of the material making up the band, etc. The act of attempting to fold a tube along its centered axis in such a way to allow it to pass through a lumen having the same or smaller diameter and yet maintain the axis of the folded stent parallel to the axis of the lumen invites plastic deformation in and of the stent.

The inventive stent uses concepts which can be thought of as widely distributing and storing the force necessary to fold the tubular stent into a configuration which will fit through a diameter smaller than its relaxed outside diameter without inducing plastic deformation of the constituent metal or plastic and yet allowing those distributed forces to expand the stent upon deployment.

Once the concept of distributing the folding or compression stresses both into a bending component (as typified by angle $\beta°$ in FIG. 4) and to twisting components (as typified by angle γ° and δ° in FIG. 4), and determining the overall size of a desired stent, determination of the optimum materials as well as the sizes of the various integral components making up the stent becomes straightforward. Specifically, the diameter and length of torsion lengths (130 and 132) and end sector (104), the number of torsion pairs (102) around the stent may then be determined.

Figure 5:
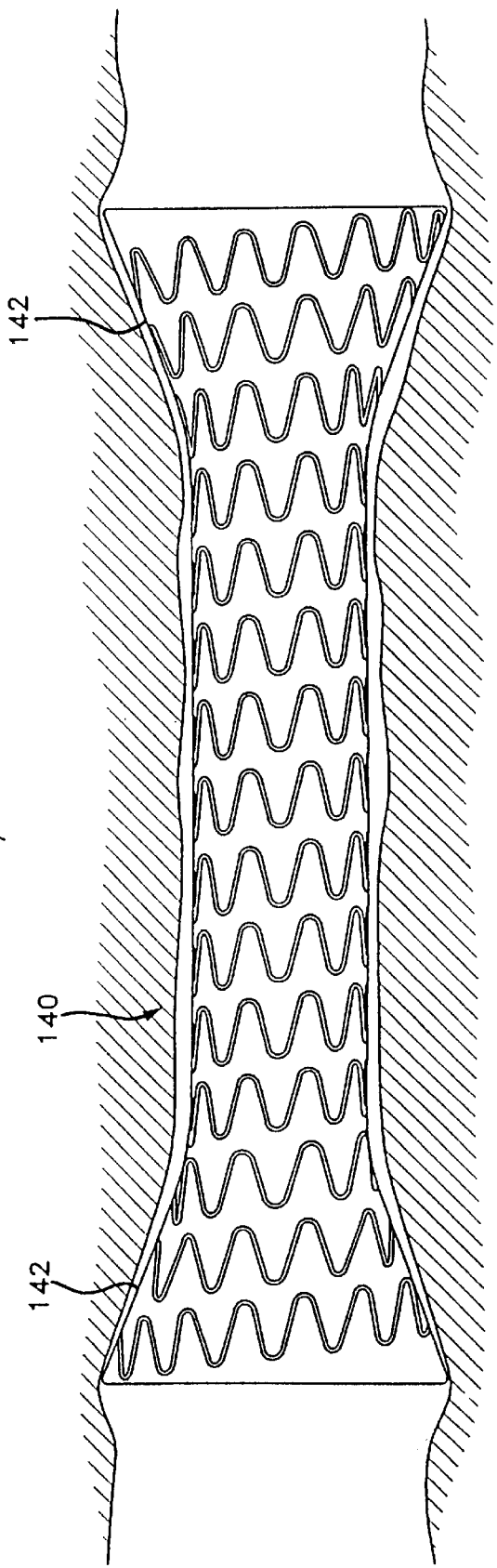
FIG. 5 is a side view of the inventive stent showing a variation having flared ends.

FIG. 5 shows, in side view, a variation of the inventive stent (140) made from wire having flares (142) at one or both ends. The flaring provides a secure anchoring of the stent or stent-graft (140) against the vessel wall. This prevents the implant from migrating downstream. In addition, the flaring provides a tight seal against the vessel so that the blood is channelled through the lumen rather than outside the graft. The undulating structure may vary in spacing to allow the helix turns to maintain its phased relationship between turns of the helix and to conform to the discussion just above. A flexible linkage between the contiguous helical turns may also be applied to at least a portion of the helices.

Figure 6:
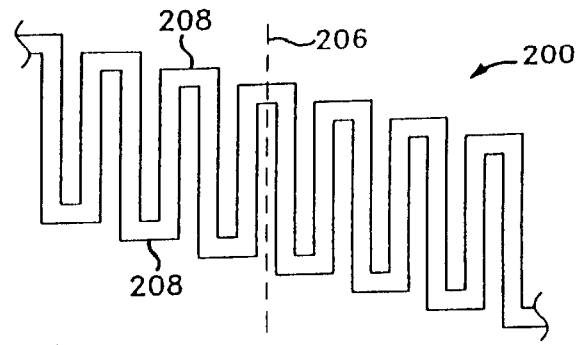
FIGS. 6, 7, and 8 show plan views of an unrolled stent produced from flat stock.
Figure 7:
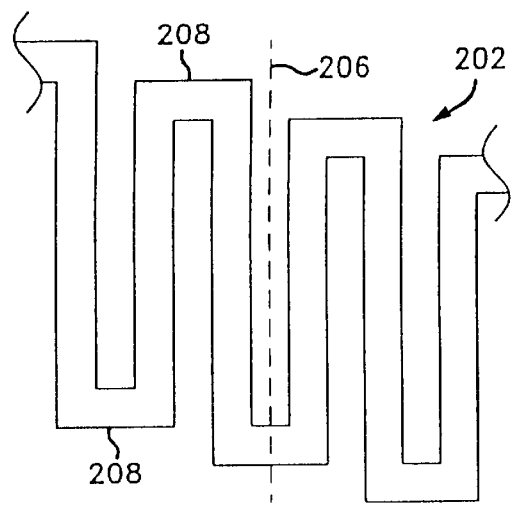
Figure 8:
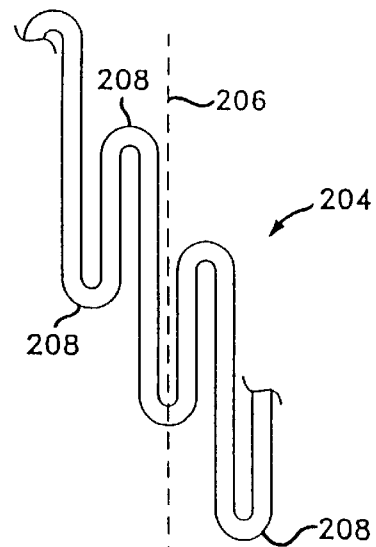
Figure 9:
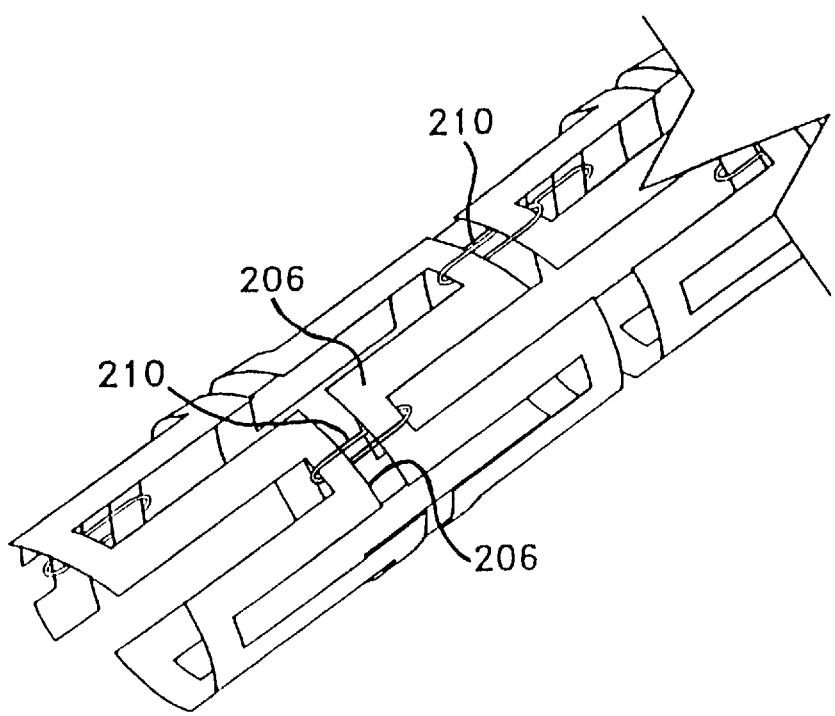
FIG. 9 shows a quarter view of the rolled stent using the flat stock pattern shown in FIG. 7.

The stent structure may also be made by forming a desired structural pattern out of a flat sheet. The sheet may then be rolled to form a tube. FIGS. 6, 7, and 8 show plan views of torsion members (respectively 200, 202, and 204) which may be then rolled about an axis (206) to form a cylinder. As is shown in FIG. 9, the end caps (208) may be aligned so that they are "out of phase". The flexible linkage (210) is then included to preserve the diameter of the stent.

The stent shown in FIG. 9 may be machined from tubing. If the chosen material in nitinol, careful control of temperature during the machining step may be had by EDM (electro-discharge-machining), laser cutting, chemical machining, or high pressure water cutting.

It should be clear that a variety of materials variously metallic, super elastic alloys, and preferably nitinol, are suitable for use in these stents. Primary requirements of the materials are that they be suitably springy even when fashioned into very thin sheets or small diameter wires. Various stainless steels which have been physically, chemically, and otherwise treated to produce high springiness are suitable as are other metal alloys such as cobalt chrome alloys (e.g., ELGILOY), platinum/tungsten alloys, and especially the nickel-titanium alloys generically known as "nitinol".

Nitinol is especially preferred because of its "super-elastic" or "pseudo-elastic" shape recovery properties, i.e., the ability to withstand a significant amount of bending and flexing and yet return to its original form without deformation. These metals are characterized by their ability to be transformed from an austenitic crystal structure to a stress-induced martensitic structure at certain temperatures, and to return elastically to the austenitic shape when the stress is released. These alternating crystalline structures provide the alloy with its super-elastic properties. These alloys are well known but are described in U.S. Pat. Nos. 3,174,851, 3,351,463, and 3,753,700. Typically, nitinol will be nominally 50.6% (±0.2%) Ni with the remainder Ti. Commercially available nitinol materials usually will be sequentially mixed, cast, formed, and separately cold-worked to 30–40%, annealed, and stretched. Nominal ultimate yield strength values for commercial nitinol are in the range of 30 psi and for Young's modulus are about 700 kBar.

The '700 patent describes an alloy containing a higher iron content and consequently has a higher modulus than the Ni-Ti alloys. Nitinol is further suitable because it has a relatively high strength to volume ratio. This allows the torsion members to be shorter than for less elastic metals. The flexibility of the stent-graft is largely dictated by the length of the torsion member components in the stent structural component. The shorter the pitch of the device, the more flexible the stent-graft structure can be made. Materials other than nitinol are suitable. Spring tempered stainless steels and cobalt-chromium alloys such as ELGILOY are also suitable as are a wide variety of other known "super-elastic" alloys.

Although nitinol is preferred in this service because of its physical properties and its significant history in implantable medical devices, we also consider it also to be suitable for use as a stent because of its overall suitability with magnetic resonance imaging (MRI) technology. Many other alloys, particularly those based on iron, are an anathema to the practice of MRI causing exceptionally poor images in the region of the alloy implant. Nitinol does not cause such problems.

Other materials suitable as the stent include certain polymeric materials, particularly engineering plastics such as thermotropic liquid crystal polymers ("LCP's"). These polymers are high molecular weight materials which can exist in a so-called "liquid crystalline state" where the material has some of the properties of a liquid (in that it can flow) but retains the long range molecular order of a crystal. The term "thermotropic" refers to the class of LCP's which are formed by temperature adjustment. LCP's may be prepared from monomers such as p,p'-dihydroxy-polynuclear-aromatics or dicarboxy-polynuclear-aromatics. The LCP's are easily formed and retain the necessary interpolymer attraction at room temperature to act as high strength plastic artifacts as are needed as a foldable stent. They are particularly suitable when augmented or filled with fibers such as those of the metals or alloys discussed below. It is to be noted that the fibers need not be linear but may have some preforming such as corrugations which add to the physical torsion enhancing abilities of the composite.

Figure 10:
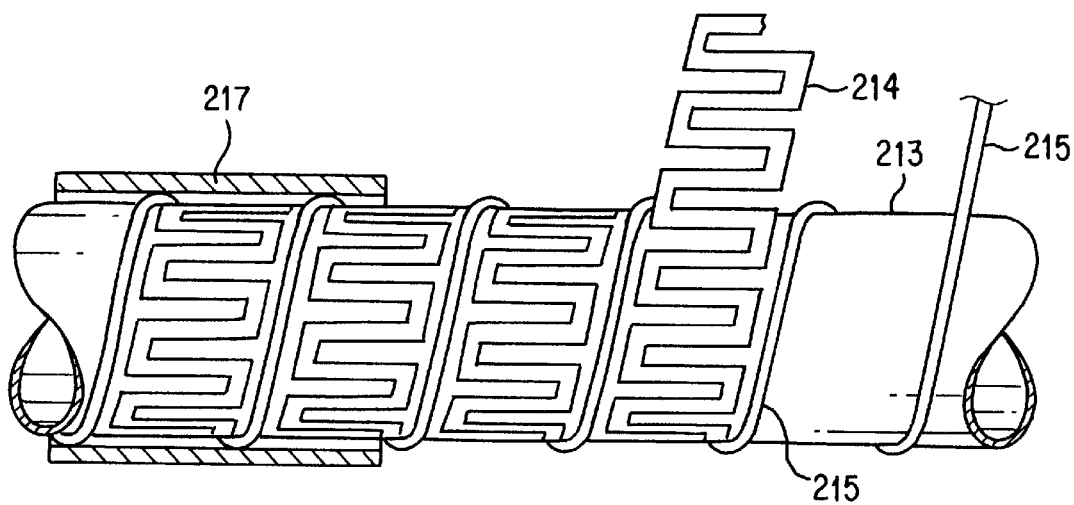
FIG. 10 shows a device for winding and heat treating a stent made according to the invention.

FIG. 10 shows a method for producing a stent of the configuration shown in FIG. 9. It may be used, of course, for producing a variety of other configurations shown herein. In this procedure, a preformed strip (211) (preferably nitinol) is rolled onto a mandrel (213) having a channel defined by a thread (215). The pitch of the strip (211) is selected using the criteria discussed above. The pitch angle (215) shown is about 20° but is not critical to the operation of the invention. Once the strip (211) is wound onto the mandrel (213) and the assembly is introduced into the outer sleeve (217), the strip (now in the shape of the stent) may then be annealed (or at least "heat set") to assist in maintaining the resulting stent in a useful shape. For use in stents of the sizes mentioned elsewhere, we have found that nitinol devices may be heat treated for five minutes or less at temperatures of 500° C. without significant lessening of the superelastic properties. Said another way, heating super-elastic alloys must carried out with some care so as not to destroy or significantly lessen the super-elastic properties.

The flexible linkage between adjacent turns of the helix (124 in FIGS. 2 and 3) may be of any appropriate filamentary material which is blood compatible or biocompatible and sufficiently flexible to allow the stent to flex and not deform the stent upon folding. Although the linkage may be a single or multiple strand wire (platinum, platinum/tungsten, gold, palladium, tantalum, stainless steel, etc.), much preferred is the use of polymeric biocompatible filaments. Synthetic polymers such as polyethylene, polypropylene, polyurethane, polyglycolic acid, polyesters, polyamides, their mixtures, blends, copolymers, mixtures, blends and copolymers are suitable; preferred of this class are polyesters such as polyethylene terephthalate including DACRON® and MYLAR® and polyaramids such as KEVLAR, polyfluorocarbons such as polytetrafluoroethylene with and without copolymerized hexafluoropropylene (TEFLON® or GORETEX), and porous or nonporous polyurethanes. Natural materials or materials based on natural sources such as collagen are especially preferred is this service.

Tubular Component

The tubular component or member of the stent-graft may be made up of any material which is suitable for use as a graft in the chosen body lumen. Many graft materials are known, particularly known are vascular graft materials. For instance, natural material may be introduced onto the inner surface of the stent and fastened into place. Synthetic polymers such as polyethylene, polypropylene, polyurethane, polyglycolic acid, polyesters, polyamides, their mixtures, blends, copolymers, mixtures, blends and copolymers are suitable; preferred of this class are polyesters such as polyethylene terephthalate including DACRON and MYLAR and polyaramids such as KEVLAR®, polyfluorocarbons such as polytetrafluoroethylene with and without copolymerized hexafluoropropylene (TEFLON® or GORETEX®), and porous or nonporous polyurethanes. Highly preferred materials are certain collagen-based materials of COLLAGEN CORPORATION of Palo Alto, Calif. The graft may adhere to or partially encapsulate or be cast about the stent when appropriate materials such as castable polyurethane or collagen-based materials are employed. When the stent-graft is produced in such a way that the openings in the stent contain graft material (as by casting), then we refer to such a stent-graft as an "integral stent-graft".

A highly preferred material is a collagen-based material described in U.S. Pat. No. 5,162,430, to Rhee et al, the entirety of which is incorporated by notice, or as described below. Collagen is easily formed into thin-walled tubes which are limp, compliant, flexible, uniform, and have smooth surfaces. The tubing walls may have a hydrated thickness of 0.001 to 0.020 inches (or to 0.100 inches in some cases) for efficacy. Other thicknesses may be used if specific goals are to be achieved. In a stent-graft, the collagen tube acts as an intravascular blood conduit to line the interior surface of the blood vessel. It isolates the lined segment of the vessel from direct contact with blood flow, tacks any tears or dissections, helps reinforce the vessel wall to protect against or isolate aneurysms, and provides a smooth, relatively thin, conformal surface for the blood flow. Of most importance (at least from the perspective of the most preferred aspects of our invention), specific collagenous materials, such as the collagen-hydrophilic polymer conjugate described in U.S. Pat. No. 5,162,430 and as described below, are very desirable as the tubular component in this stent-graft in that they form non-thrombogenic surfaces which will support the growth of endothelium.

The preferred collagen composition used in this invention is a pharmaceutically acceptable non-immunogenic composition formed by covalently binding atelopeptide collagen to pharmaceutically pure, synthetic, hydrophilic polymers via specific types of chemical bonds to provide collagen/polymer conjugates. Any type of collagen may be used including extracted and purified collagen including atelopeptide collagen which can be type I, type II or type III collagen. The collagen may be extracted from various sources such as bovine hide and human placenta and may be fibrillar or non-fibrillar. The synthetic hydrophilic polymer may be polyethylene glycol and derivatives thereof having a weight average molecular weight over a range of from about 100 to about 20,000. The compositions may incorporate other components such as biologically active materials. The collagen-polymer conjugates generally contain large amounts of water when formed. The extruded materials may be dehydrated, resulting in a reasonably flexible material which can be readily stored.

The term "collagen" as used herein refers to all forms of collagen, including those which have been extracted, processed or otherwise modified. Preferred collagens are non-immunogenic and, if extracted from animals, are treated to remove the immunogenic telopeptide regions ("atelopeptide collagen"), are soluble, and may be in the fibrillar or non-fibrillar form. Type I collagen is best suited to most applications involving bone or cartilage repair. However, other forms of collagen are also useful in the practice of the invention, and are not excluded from consideration here. Collagen crosslinked using heat, radiation, or chemical agents such as glutaraldehyde may be conjugated with polymers as described herein to form particularly rigid compositions. Collagen crosslinked using glutaraldehyde or other (nonpolymer) linking agents is referred to herein as "GAX", while collagen crosslinked using heat and/or radiation is termed "HRX." Collagen used in connection with the preferred embodiments of the invention is in a pharmaceutically pure form such that it can be incorporated into a body, human or otherwise, for the intended purpose.

The term "synthetic hydrophilic polymer" as used herein refers to a synthetic polymer having an average molecular weight and composition which renders the polymer essentially water-soluble. Preferred polymers are highly pure or are purified to a highly pure state such that the polymer is, or is treated to become, pharmaceutically pure. Most hydrophilic polymers can be rendered water-soluble by incorporating a sufficient number of oxygen (or, less frequently, nitrogen) atoms available for forming hydrogen bonds in aqueous solutions. Preferred polymers are hydrophilic but not soluble. Preferred hydrophilic polymers used herein include polyethylene glycol, polyoxyethylene, polymethylene glycol, polytrimethylene glycols, polyvinylpyrrolidones, and derivatives thereof. The polymers can be linear or multiply branched and will not be substantially crosslinked. Other suitable polymers include polyoxyethylene-polyoxypropylene block polymers and copolymers. Polyoxyethylene-polyoxypropylene block polymers having an ethylene diamine nucleus (and thus having four ends) are also available and may be used in the practice of the invention. Naturally occurring and/or biologically active polymers such as proteins, starch, cellulose, heparin, and the like are not generally desirable in this definition although they may be used. All suitable polymers will be non-toxic, non-inflammatory and non-immunogenic when used to form the desired composition, and will preferably be essentially non-degradable in vivo over a period of at least several months. The hydrophilic polymer may increase the hydrophilicity of the collagen, but does not render it water-soluble. Presently preferred hydrophilic polymers are mono-, di-, and multi-functional polyethylene glycols (PEG). Monofunctional PEG has only one reactive hydroxy group, while difunctional PEG has reactive groups at each end. Monofunctional PEG preferably has a weight average molecular weight between about 100 and about 15,000, more preferably between about 200 and about 8,000, and most preferably about 4,000. Difunctional PEG preferably has a molecular weight of about 400 to about 40,000, more preferably about 3,000 to about 10,000. Multi-functional PEG preferably has a molecular weight between about 3,000 and 100,000.

PEG can be rendered monofunctional by forming an alkylene ether at one end. The alkylene ether may be any suitable alkoxy radical having 1–6 carbon atoms, for example, methoxy, ethoxy, propoxy, 2-propoxy, butoxy, hexyloxy, and the like. Methoxy is presently preferred. Difunctional PEG is provided by allowing a reactive hydroxy group at each end of the linear molecule. The reactive groups are preferably at the ends of the polymer, but may be provided along the length thereof.

The term "chemically conjugated" as used herein means attached through a covalent chemical bond. In the practice of the invention, a synthetic hydrophilic polymer and collagen may be chemically conjugated by using a linking radical, so that the polymer and collagen are each bound to the radical, but not directly to each other. The term "collagen-polymer" refers to collagen chemically conjugated to a synthetic hydrophilic polymer, within the meaning of this invention. Thus, "collagen-PEG" (or "PEG-collagen") denotes a composition within the most preferred aspect of the invention wherein collagen is chemically conjugated to PEG. "Collagen-dPEG" refers to collagen chemically conjugated to difunctional PEG, wherein the collagen molecules are typically crosslinked. "Crosslinked collagen" refers to collagen in which collagen molecules are linked by covalent bonds with polyfunctional (including difunctional) polymers. Terms such as "GAX-dPEG" and "HRX-dPEG" indicate collagen crosslinked by both a difunctional hydrophilic polymer and a crosslinking agent such as glutaraldehyde or heat. The polymer may be "chemically conjugated" to the collagen by means of a number of different types of chemical linkages. For example, the conjugation can be via an ester or urethane linkage, but is more preferably by means of an ether linkage. An ether linkage is preferred in that it can be formed without the use of toxic chemicals and is not readily susceptible to hydrolysis in vivo.

Those of ordinary skill in the art will appreciate that synthetic polymers such as polyethylene glycol cannot be prepared practically to have exact molecular weights, and that the term "molecular weight" as used herein refers to the weight average molecular weight of a number of molecules in any given sample, as commonly used in the art. Thus, a sample of PEG 2,000 might contain a statistical mixture of polymer molecules ranging in weight from, for example, 1,500 to 2,500 daltons with one molecule differing slightly from the next over a range. Specification of a range of molecular weight indicates that the average molecular weight may be any value between the limits specified, and may include molecules outside those limits. Thus, a molecular weight range of about 800 to about 20,000 indicates an average molecular weight of at least about 800, ranging up to about 20 kDa.

The term "available lysine residue" as used herein refers to lysine side chains exposed on the outer surface of collagen molecules, which are positioned in a manner to allow reaction with activated PEG. The number of available lysine residues may be determined by reaction with sodium 2,4,6-trinitrobenzenesulfonate (TNBS).

The term "growth factor" is used to describe biologically active molecules and active peptides (which may be naturally occurring or synthetic) which aid in healing or regrowth of normal tissue. The function of growth factors is two-fold: 1) they can incite local cells to produce new collagen or tissue, or 2) they can attract cells to the site in need of correction. As such, growth factors may serve to encourage "biological anchoring" of the collagen graft implant within the host tissue. As previously described, the growth factors may either be admixed with the collagen-polymer conjugate or chemically coupled to the conjugate. For example, one may incorporate growth factors such as epidermal growth factor (EGF), transforming growth factor (TGF) alpha, TGF$_\beta$ (including any combination of TGF$_\beta$s), TGF$_{\beta 1}$, TGF$_{\beta 2}$, platelet derived growth factor (PDGF-AA, PDGF-AB, PDGF-BB), acidic fibroblast growth factor (FGF), basic FGF, connective tissue activating peptides (CTAP), $\beta$-thromboglobulin, insulin-like growth factors, erythropoietin (EPO), nerve growth factor (NGF), bone morphogenic protein (BMP), osteogenic factors, and the like. Incorporation of growth factors can facilitate regrowth when the tubes are used in the treatment of defective or damaged channels. Furthermore, one may chemically link the growth factors to the collagen-polymer composition by employing a suitable amount of multi-functional polymer molecules during synthesis. The growth factors may then be attached to the free polymer ends by the same method used to attach PEG to collagen, or by any other suitable method. By tethering growth factors to the outer and/or inner surface of the graft material, the amount of grafts needed to carry out effective treatment is substantially reduced. Tubes which incorporate growth factors may provide effective controlled-release drug delivery. By varying the chemical linkage between the collagen and the synthetic polymer, it is possible to vary the effect with respect to the release of the biologic. For example, when an "ester" linkage is used, the linkage is more easily broken under physiological conditions, allowing for sustained release of the growth factor from the matrix. However, when an "ether" linkage is used, the bonds are not easily broken and the growth factor will remain in place for longer periods of time with its active sites exposed providing a biological effect on the natural substrate for the active site of the protein. It is possible to include a mixture of conjugates with different linkages so as to obtain variations in the effect with respect to the release of the biologic, e.g., the sustained release effect can be modified to obtain the desired rate of release.

The terms "effective amount" or "amount effective to treat" refer to the amount of composition required in order to obtain the effect desired. Thus, a "tissue growth-promoting amount" of a composition containing a growth factor refers to the amount of growth factor needed in order to stimulate tissue growth to a detectable degree. Tissue, in this context, includes connective tissue, bone, cartilage, epidermis and dermis, blood, and other tissues with particular emphasis on tissues which form channels such as veins, arteries, intestines and the like. The actual amount which is determined to be an effective amount will vary depending on factors such as the size, condition, sex, and age of the patient, the type of tissue or channel, the effect desired and type of growth factor, and can be more readily determined by the caregiver.

The term "sufficient amount" as used herein is applied to the amount of carrier used in combination with the collagen-polymer conjugates used in forming the tubes of the invention. A sufficient amount is that amount which, when mixed with the conjugate, renders it in the physical form desired, for example, extrudable tubes, extrudable cylinders having any desired cross-section, and so forth. Extrudable formulations may include an amount of a carrier sufficient to render the composition smoothly extrudable without significant need to interrupt the extrusion process. The amount of the carrier can be varied and adjusted depending on the size and shape and thickness of the wall of the tube being extruded. Such adjustments will be apparent to those skilled in the art upon reading this disclosure.

Conjugates

To form the most desired collagen-conjugates used in the inventive stent-grafts, collagen must be chemically bound to a synthetic hydrophilic polymer. This can be carried out in a variety of ways. In accordance with the preferred method, the synthetic hydrophilic polymer is activated and then reacted with the collagen. Alternatively, the hydroxyl or amino groups present on the collagen can be activated and the activated groups will react with the polymer to form the conjugate. In accordance with a less preferred method, a linking group with activated hydroxyl or amino groups thereon can be combined with the polymer and collagen in a manner so as to concurrently react with both the polymer and collagen forming the conjugate. Other methods of forming the conjugates will become apparent to those skilled in the art upon reading this disclosure. Since the conjugates of the invention are to be used in the human body it is important that all of the components, including the polymer, collagen, and linking group, if used form a conjugate that is unlikely to be rejected by the body. Accordingly, toxic and/or immunoreactive components are not preferred as starting materials. Some preferred starting materials and methods of forming conjugates are described further below.

Although different hydrophilic synthetic polymers can be used in connection with forming the conjugate, such polymers must be biocompatible, relatively insoluble, but hydrophilic and is preferably one or more forms of polyethylene glycol (PEG), due to its known biocompatibility. Various forms of PEG are extensively used in the modification of biologically active molecules because PEG can be formulated to have a wide range of solubilities and because it lacks toxicity, antigenicity, immunogenicity, and does not typically interfere with the enzymatic activities and/or conformations of peptides. Further, PEG is generally non-biodegradable and is easily excreted from most living organisms including humans.

The first step in forming the collagen-polymer conjugates generally involves the functionalization of the PEG molecule. Various functionalized polyethylene glycols have been used effectively in fields such as protein modification (see Abuchowski et al., *Enzymes as Drugs,* John Wiley & Sons; New York, N.Y. (1981) pp. 367–383; and Dreborg et al., *Crit. Rev. Therap. Drug Carrier Syst.* (1990) 6:315, both of which are incorporated herein by reference), peptide chemistry (see Mutter et al., *The Peptides,* Academic: New York, N.Y. 2:285–332; and Zalipsky et al., *Int. J. Peptide Protein Res.* (1987) 30:740, both of which are incorporated herein by reference), and the synthesis of polymeric drugs (see Zalipsky et al., *Eur. Polym. J.* (1983) 19:1177; and Ouchi et al., *J. Macromol. Sci. -Chem.* (1987) A24:1011, both of which are incorporated herein by reference). Various types of conjugates formed by the binding of polyethylene glycol with specific pharmaceutically active proteins have been disclosed and found to have useful medical applications in part due to the stability of such conjugates with respect to proteolytic digestion, reduced immunogenicity and longer half-lives within living organisms.

One form of polyethylene glycol which has been found to be particularly useful is monomethoxypolyethylene glycol (mPEG), which can be activated by the addition of a compound such as cyanuric chloride, then coupled to a protein (see Abuchowski et al., *J. Biol. Chem.* (1977) 252:3578, which is incorporated herein by reference). Although such methods of activating polyethylene glycol can be used in connection with the present invention, they are not particularly desirable in that the cyanuric chloride is relatively toxic and must be completely removed from any resulting product in order to provide a pharmaceutically acceptable composition.

Activated forms of PEG can be made from reactants which can be purchased commercially. One form of activated PEG which has been found to be particularly useful in connection with the present invention is mPEG-succinate-N-hydroxysuccinimide ester (SS-PEG) (see Abuchowski et al., *Cancer Biochem. Biphys.* (1984) 7:175, which is incorporated herein by reference). Activated forms of PEG such as SS-PEG react with the proteins under relatively mild conditions and produce conjugates without destroying the specific biological activity and specificity of the protein attached to the PEG. However, when such activated PEGs are reacted with proteins, they react and form linkages by means of ester bonds. Although ester linkages can be used in connection with the present invention, they are not particularly preferred in that they undergo hydrolysis when subjected to physiological conditions over extended periods of time (see Dreborg et al., *Crit. Rev. Therap. Drug Carrier Syst.* (1990) 6:315; and Ulbrich et al., *J. Makromol. Chem.* (1986) 187:1131, both of which are incorporated herein by reference).

It is possible to link PEG to proteins via urethane linkages, thereby providing a more stable attachment which is more resistant to hydrolytic digestion than the ester linkages (see Zalipsky et al., Polymeric Drug and Drug Delivery Systems, Chapter 10, "Succinimidyl Carbonates of Polyethylene Glycol" (1991) incorporated herein by reference to disclose the chemistry involved in linking various forms of PEG to specific biologically active proteins). The stability of urethane linkages has been demonstrated under physiological conditions (see Veronese et al., *Appl. Biochem. Biotechnol.* (1985) 11:141; and Larwood et al., *J. Labelled Compounds Radiopharm.* (1984) 21:603, both of which are incorporated herein by reference). Another means of attaching the PEG to a protein can be by means of a carbamate linkage (see Beauchamp et al., *Anal. Biochem.* (1983) 131:25; and Berger et al., *Blood* (1988) 71:1641, both of which are incorporated herein by reference). The carbamate linkage is created by the use of carbonyldiimidazole-activated PEG. Although such linkages have advantages, the reactions are relatively slow and may take 2 to 3 days to complete.

The various means of activating PEG described above and publications (all of which are incorporated herein by reference) cited in connection with the activation means are described in connection with linking the PEG to specific biologically active proteins and not collagen. However, the present invention now discloses that such activated PEG compounds can be used in connection with the formation of collagen-PEG conjugates. Such conjugates provide a range of improved characteristics and as such can be used to form the various compositions used in forming the tubes of the present invention. [*Polymeric Drug and Drug Delivery Systems,* Chapter 10, "Succinimidyl Carbonates of Polyethylene Glycol" (1991), incorporated herein by reference to disclose the chemistry involved in linking various forms of PEG to specific biologically active proteins.]

As indicated above, the conjugates used in forming the grafts may be prepared by covalently binding a variety of different types of synthetic hydrophilic polymers to collagen. However, because the final product or conjugate obtained must have a number of required characteristics such as being extrudable from a nozzle, biocompatible and non-immunogenic, it has been found useful to use polyethylene glycol as the synthetic hydrophilic polymer. The polyethylene glycol must be modified in order to provide activated groups on one or preferably both ends of the molecule so that covalent binding can occur between the PEG and the collagen. Some specific functionalized forms of PEG are shown structurally below, as are the products obtained by reacting these functionalized forms of PEG with collagen.

The first functionalized PEG is difunctionalized PEG succinimidyl glutarate, referred to herein as (SG-PEG). The structural formula of this molecule and the reaction product obtained by reacting it with collagen is shown in Formula 1.

FORMULA 1

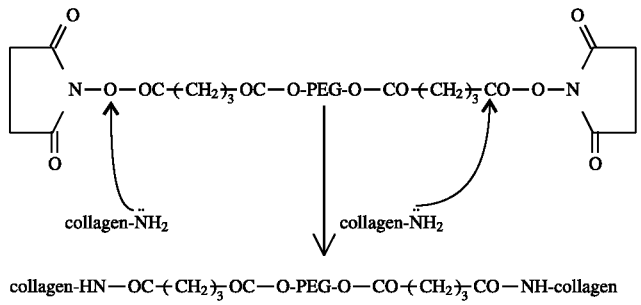

Another difunctionally activated form of PEG is referred to as PEG succinimidyl (S-PEG). The structural formula for this compound and the reaction product obtained by reacting it with collagen is shown in Formula 2. In a general structural formula for the compound of Formula 2, the subscript 3 is replaced with an "n." In the embodiment shown in Formula 1, n=3, in that there are three repeating $CH_2$ groups on each side of the PEG. The structure in Formula 2 results in a conjugate which includes an "ether" linkage which is not subject to hydrolysis. This is distinct from the first conjugate shown in Formula 1, wherein an ester linkage is provided. The ester linkage is subject to hydrolysis under physiological conditions.

S-PEG, n = 3: Difunctional PEG Succinimidyl

FORMULA 2

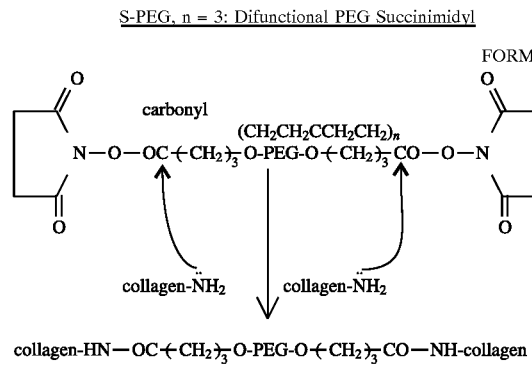

Yet another derivatized form of polyethylene glycol, wherein n=2 is shown in Formula 3, as is the conjugate formed by reacting the derivatized PEG with collagen.

S-PEG, n = 2: Difunctional PEG Succinimidyl

FORMULA 3

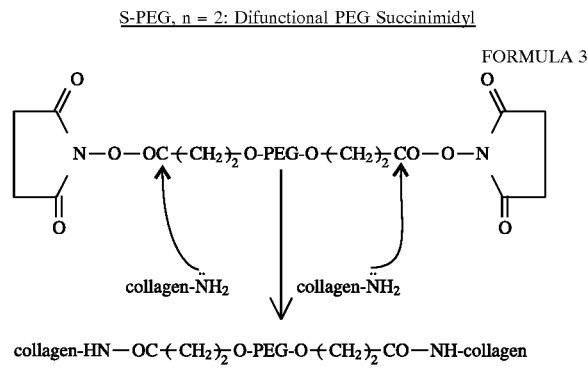

Another preferred embodiment of the invention similar to the compounds of Formula 2 and Formula 3, is provided when n=1. The structural formula and resulting conjugate are shown in Formula 4. It is noted that the conjugate includes both an ether and a peptide linkage. These linkages are stable under physiological conditions.

S-PEG, n = 1: Difunctional PEG Succinimidyl

FORMULA 4

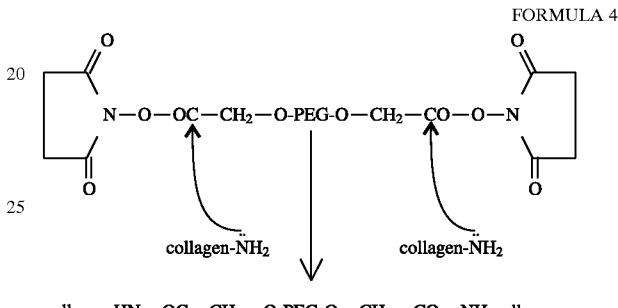

Yet another derivatized form of PEG is provided when n=0. The difunctionalized form is referred to as PEG succinimidyl carbonate (SC-PEG). The structural formula of this compound and the conjugate formed by reacting SC-PEG with collagen is shown in Formula 5. Although this conjugate includes a urethane linkage, the conjugate has been found not to have a high degree of stability under physiological conditions. The instability can be a desirable characteristic when the tubes are used in a situation where it is desirable that they dissolve over time.

SC-PEG, n = 0: Difunctional PEG Succinimidyl Carbonate

FORMULA 5

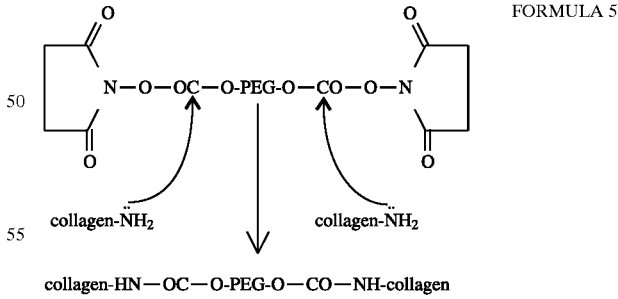

All of the derivatives depicted in Formulas 1–5 involve the inclusion of the succinimidyl group. However, different activating groups can be attached to one or both ends of the PEG. For example, the PEG can be derivatized to form difunctional PEG propionaldehyde (A-PEG), which is shown in Formula 6, as is the conjugate formed by the reaction of A-PEG with collagen.

A-PEG: Difunctional PEG Propion Aldehyde

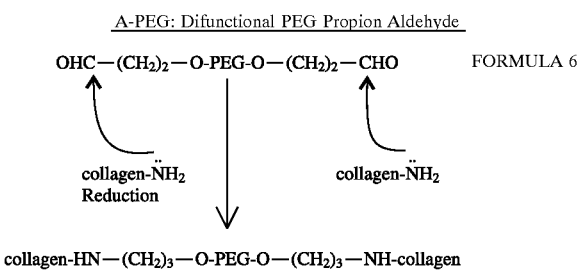

FORMULA 6 collagen-HN—(CH$_2$)$_3$—O-PEG-O—(CH$_2$)$_3$—NH-collagen

Yet another functionalized form of polyethylene glycol is difunctional PEG glycidyl ether (E-PEG), which is shown in Formula 7, as

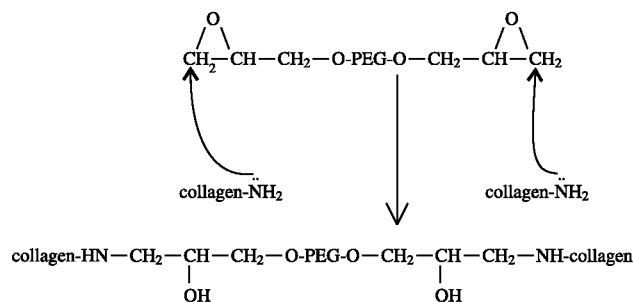

collagen-HN—CH$_2$—CH—CH$_2$—O-PEG-O—CH$_2$—CH—CH$_2$—NH-collagen
               |                                         |
              OH                                   OH The conjugates formed using the functionalized forms of PEG vary depending on the functionalized form of PEG which is used in the reaction. Furthermore, the final product can be varied with respect to its characteristics by changing the molecular weight of the PEG. In general, the stability of the conjugate is improved by eliminating any ester linkages between the PEG and the collagen and including ether and/or urethane linkages. These stable linkages are generally used to form tubes to replace or augment a channel as may be done with a stent-graft. When the grafts are used as a temporary repair unit for a damaged channel, it may be desirable to include the weaker ester linkages so that the linkages are gradually broken by hydrolysis under physiological conditions, breaking apart the tube as it may be replaced by host tissue, or as it degrades, and releasing a component held therein, such as a growth factor. By varying the chemical structure of the linkage, the rate of sustained release can be varied.

Suitable collagens include all types of pharmaceutically useful collagen, preferably types I, II and III. Collagens may be soluble (for example, commercially available Vitrogen® 100 collagen-in-solution), and may or may not have the telopeptide regions. Preferably, the collagen will be reconstituted fibrillar atelopeptide collagen, for example Zyderm® collagen implant (ZCI) or atelopeptide collagen in solution (CIS). Various forms of collagen are available commercially, or may be prepared by the processes described in, for example, U.S. Pat. Nos. 3,949,073; 4,488,911; 4,424,208; 4,582,640; 4,642,117; 4,557,764; and 4,689,399, all incorporated herein by reference. Fibrillar, atelopeptide, reconstituted collagen is preferred in order to form tubes used for the repair or augmentation of channels.

Compositions used in forming the invention comprise collagen chemically conjugated to a selected synthetic hydrophilic polymer or polymers. Collagen contains a number of available amino and hydroxy groups which may be used to bind the synthetic hydrophilic polymer. The polymer may be bound using a "linking group", as the native hydroxy or amino groups in collagen and in the polymer frequently require activation before they can be linked. For example, one may employ compounds such as dicarboxylic anhydrides (e.g., glutaric or succinic anhydride) to form a polymer derivative (e.g., succinate), which may then be activated by esterification with a convenient leaving group, for example, N-hydroxysuccinimide, N,N'-disuccinimidyl oxalate, N,N'-disuccinimidyl carbonate, and the like. See also Davis, U.S. Pat. No. 4,179,337 for additional linking groups. Presently preferred dicarboxylic anhydrides that are used to form polymer-glutarate compositions include glutaric anhydride, adipic anhydride, 1,8-naphthalene dicarboxylic anhydride, and 1,4,5,8-naphthalenetetracarboxylic dianhydride. The polymer thus activated is then allowed to react with the collagen, forming a collagen-polymer composition used to make the grafts.

FORMULA 7

In one highly desirable embodiment having ester linkages, a pharmaceutically pure form of monomethylpolyethylene glycol (MPEG) (mw 5,000) is reacted with glutaric anhydride (pure form) to create mPEG glutarate. The glutarate derivative is then reacted with N-hydroxysuccinimide to form a succinimidyl monomethylpolyethylene glycol glutarate. The succinimidyl ester (mPEG*, denoting the activated PEG intermediate) is then capable of reacting with free amino groups present on collagen (lysine residues) to form a collagen-PEG conjugate wherein one end of the PEG molecule is free or nonbound. Other polymers may be substituted for the monomethyl PEG, as described above. Similarly, the coupling reaction may be carried out using any known method for derivatizing proteins and synthetic polymers. The number of available lysines conjugated may vary from a single residue to 100% of the lysines, preferably 10–50%, and more preferably 20–30%. The number of reactive lysine residues may be determined by standard methods, for example by reaction with TNBS.

The resulting product is a smooth, pliable, rubbery mass having a shiny appearance. It may be wetted, but is not water-soluble. It may be formulated as a suspension at any convenient concentration, preferably about 30–65 mg/mL, and may be extruded through a nozzle to form a tube. The consistency of the formulation may be adjusted by varying the amount of liquid used.

Figure 11:
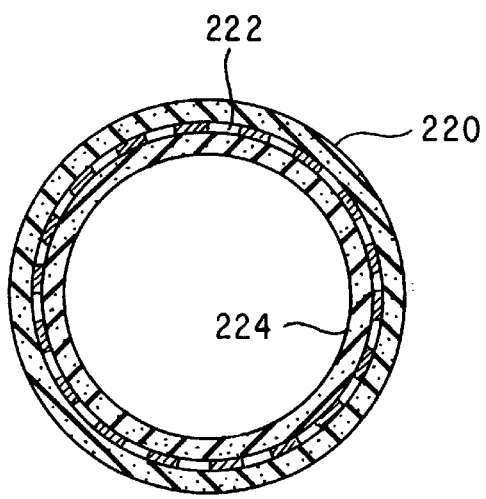
FIGS. 11 and 12 show end view cutaways of stent-grafts made according to the invention.

The tubular component, whether collagen-based or not, may be reinforced using a network of small diameter fibers. The fibers may be random, braided, knitted, or woven. The fibers may be imbedded in the tubular component wall, may be placed in a separate layer coaxial with the tubular component, or may be used in a combination of the two. FIG. 11 shows an end view, cross-section of the configuration in which the stent (220) forms the outermost layer, a fibrous layer (222) coaxial to and inside the stent (220), and the tubular component (224) of, e.g., collagen as the inner layer.

Figure 12:
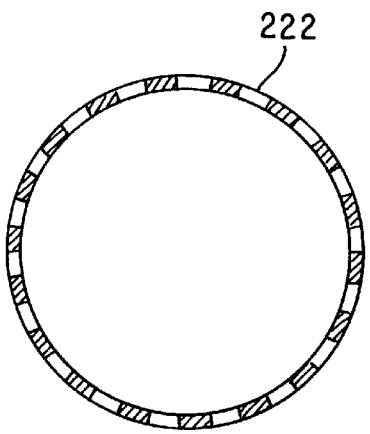

Particularly desirable is the variation shown in FIG. 12 in which the fibrous material is mixed with or imbedded into the tubular layer (226) and cast or injected around the stent (220). This fibrous material may extend for the length of the device or may be shorter. The fibers may be wound or placed in any reasonable orientation within the device. Alternatively, randomly oriented short segments of fibers may also be imbedded in the wall of the tubing. The fiber may be any suitable fibrous blood-compatible material including polyesters such as DACRON®, polyamides such as NYLON, KEVLAR®, polyglycolic acids, polylactic acids, polyethylene, polypropylene, silk or other strong flexible fiber which are not detrimentally affected in the medical service in which this device is placed. Specifically, polypropylene and the like will not be dissolved in blood but polyglycolic acid will dissolve. Each are suitable but work in different ways.

In addition, one or more radio-opaque metallic fibers, such as gold, platinum, platinum-tungsten, palladium, platinum-iridium, rhodium, tantalum, or alloys or composites of these metals like may be incorporated into the multi-strand reinforcement network to allow fluoroscopic visualization of the device.

In the collagen-fiber composite tube, the fibers carry much of the hoop stress and other loadings imposed by the vessel. This relieves the loading on the collagen and significantly increases the burst strength and fatigue properties of the tube. In addition, this makes the tube more effective in hydraulically isolating the vessel and as a result prevents the formation or worsening of aneurysms. This would be particularly beneficial in thinned weakened vessel walls resulting from de-bulking interventions or from medial thinning that has been seen to accompany stent placement. Another benefit of the fiber reinforcement is the increase in resistance to radially inward loading, especially if the loading is very focussed. Finally, fiber reinforcement may also impart some longitudinal stiffness to the stent-graft. This allows the stent-graft to maintain its strength and prevent it from kinking or sagging into the lumen.

Production of the Stent-Graft

The preferred method of constructing the stent-graft is to first construct the stent and then to mold or cast the collagen tubular component about the stent.

The stent structure and fiber reinforcement may be molded into the wall of the collagen tube. A mold for such a structure desirably is a simple annular space between two cylinders having room in the annular space for placement of the stent and would have a longitudinal axis slightly longer than the length of the stent-graft to be produced. The stent and fiber tubing is centered in the annular space and then the remaining space filled with collagen. If sPEG cross-linked collagen is used as the matrix material, the sPEG and collagen are mixed and introduced into the mold and allowed to cure. After curing, the mold is separated and the inventive fiber reinforced collagen tube with a stent structure produced.

Deployment of the Invention

When a stent-graft having torsion members is folded, crushed, or otherwise collapsed, mechanical energy is stored in torsion in those torsion members. In this loaded state, the torsion members have a torque exerted about them and consequently have a tendency to untwist. Collectively, the torque exerted by the torsion members as folded down to a reduced diameter must be restrained from springing open. The stent typically has at least one torsion member per fold to take advantage of the invention. The stent-graft is folded along its longitudinal axis and restrained from springing open. The stent-graft is then deployed by removing the restraining mechanism, thus allowing the torsion members to spring open against the vessel wall.

The attending surgeon will choose a stent or stent-graft having an appropriate diameter. However, inventive devices of this type are typically selected having an expanded diameter of up to about 10% greater than the diameter of the lumen to be the site of the stent deployment.

FIG. 13A shows a sequence of folding the device (230) of this invention about a guidewire (232) into a loose C-shaped configuration. FIG. 13B shows a front quarter view of the resulting folded stent or stent-graft.

FIG. 13C shows a sequence of folding the device (230) of this invention about a guidewire (232) into a rolled configuration. FIG. 13D shows a front quarter view of the resulting folded stent or stent-graft.

FIG. 13E shows a sequence of folding the device (230) of this invention about a guidewire (232) into a triple lobed configuration. FIG. 13F shows a front quarter view of the resulting folded stent or stent-graft.

The stent-graft may be tracked through the vasculature to the intended deployment site and then unfolded against the vessel lumen. The collagen tube component of the stent-graft is limp, flexible, and thus easy to fold. Folding of the stent structure in the manner discussed above allows it to return to a circular, open configuration.

Figure 14A:
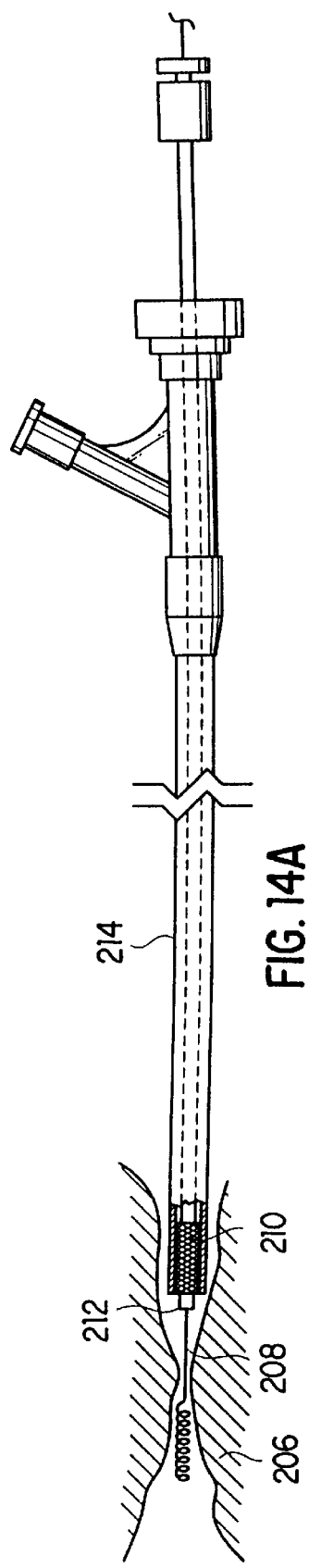
FIGS. 14A–14C show a schematic procedure for deploying the inventive stent-grafts using an external sleeve.
Figure 14B:
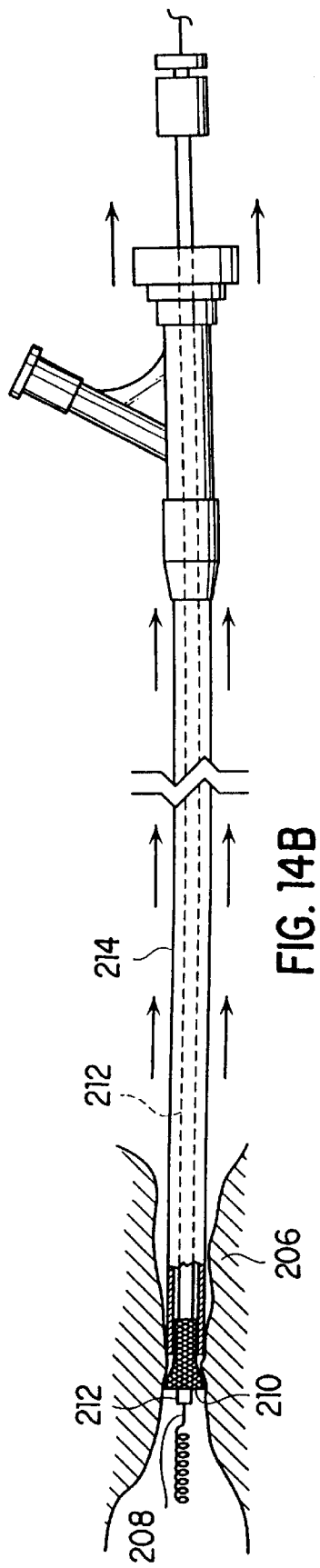
Figure 14C:
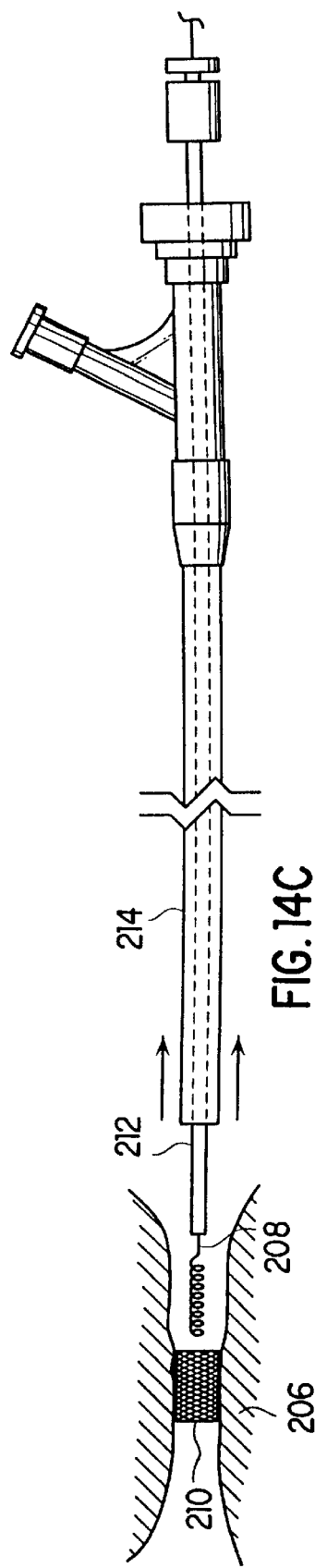

FIGS. 14A–14C show one desired way to place the devices of the present invention and allow them to self-expand. FIG. 14A shows a target site (246) having, e.g., a narrowed vessel lumen. A guidewire (248) having a guide tip (250) has been directed to the site using known techniques. The stent-graft (252) is mounted on guidewire tubing (254) inside outer sliding sheath (256) after having folded in the manner discussed above. The outer sliding sheath (256) binds the compressed stent-graft (252) in place until released.

FIG. 14B shows placement of the stent-graft (252) at the selected site (246) by sliding the stent-graft (252) over the guidewire (248) all together with the guidewire tubing (254) and the outer sliding sheath (256). The stent-graft (252) is deployed by holding the guidewire tubing (254) in a stationary position while withdrawing the outer sliding sheath (256). The stent-graft (252) can be seen in FIG. 14B as partially deployed.

FIG. 14C shows the stent-graft (252) fully deployed after the guidewire tubing (254) and the outer sliding sheath (256) have been fully retracted.

FIGS. 15A–C, 16A–C, and 17A–C show an inventive variation of deploying a stent or stent-graft made according to this invention. These methods involve the use of a control line or tether line which maintains the stent or stent-graft in a folded configuration until release.

FIG. 15A is a front-quarter view of the stent (302) or stent-graft which has been folded as shown in the Figures discussed above. The stent (302) is folded about guidewire (304) so that, when deployed, the guidewire (304) is within the stent (302). Central to the variation shown here is the tether wire (306) which is passed through loops (308) associated with the various helices as they wind about the stent (302). The loops (308) may be formed from the flexible link (124 in FIGS. 2 or 3) or may be simply an alternating weave through appropriate apexes of the undulating helix, e.g., (104 in FIG. 3) or may be loops specifically installed for the purpose shown here. It should be clear that the tether wire (306) is so placed that when it is removed by sliding it axially along the stent (302) and out of the loops (308), that the stent (302) unfolds into a generally cylindrical shape within the body lumen.

FIG. 15B shows an end-view of a folded stent (302) or stent-graft having a guidewire (304) within the inner surface of the stent (302) and with the tether wire (306) within the loops (308). The end view of the folded stent (302) shows it to be folded into a form which is generally C-shaped. When expanded by removal of the tether wire (306), the stent (302) in FIG. 15B assumes the form shown in end view in FIG. 15C. There may be seen the guidewire (304) within the lumen of the stent (302) and the loops (308) which were formerly in a generally linear relationship having a tether wire passing through them.

FIG. 16A shows a folded stent (310) (or stent-graft) in front quarter view which is similar in configuration to the stent (302) shown in FIG. 15A except that the stent (310) is rolled somewhat tighter than the previously discussed stent. The guidewire (304) is also inside the stent (310) rather than outside of it. Loops (308) from generally opposing sides of the stent (310) are folded into an approximate line so that the tether wire may pass through the aligned loops (308). FIG. 16B shows an end view of the stent (310), and in particular, emphasizes the tighter fold of the stent (310). When expanded by removal of the tether wire (306), the stent (310) in FIG. 16B assumes the form shown in FIG. 16C. In FIG. 16C may be seen the guidewire (304) within the lumen of the stent (310) and the loops (308) which were formerly in a generally linear relationship having a tether wire passing through them.

FIGS. 17A–C show a schematic procedure for deploying the stent (312) (or stent-graft) using a percutaneous catheter assembly (314).

In FIG. 17A may be seen a percutaneous catheter assembly (314) which has been inserted to a selected site (316) within a body lumen. The stent (312) is folded about the guidewire (319) and guidewire tube (318) held axially in place prior to deployment by distal barrier (320) and proximal barrier (322). The distal barrier (320) and proximal barrier (322) typically are affixed to the guidewire tube (318). The tether wire (306) is shown extending through loops (308) proximally through the catheter assembly's (314) outer jacket (324) through to outside the body.

FIG. 17B shows the removal of the tether wire (306) from a portion of the loops (308) to partially expand the stent (312) onto the selected site (316).

FIG. 17C shows the final removal of the tether wire (306) from the loops (308) and the retraction of the catheter assembly (314) from the interior of the stent (312). The stent (312) is shown as fully expanded.

Many alterations and modifications may be made by those of ordinary skill in the art without departing from the spirit and scope of the invention. The illustrated embodiments have been shown only for purposes of clarity and examples, and should not be taken as limiting the invention as defined by the following claims, which include all equivalents, whether now or later devised.

We claim as our invention:

1. A device comprising:
   a tubular stent defined by a helically arranged undulating member containing multiple turns about a common longitudinal axis, said undulating member containing a plurality of open unconfining undulations each having an amplitude; and
   a coupling member extending through undulations of adjacent turns and movable along the undulations over a substantial portion of said amplitude.

2. The device of claim 1 further including a coaxially positioned, polymeric tubular graft coupled to said stent.

3. The device of claim 2, wherein said stent is formed from a self-expanding elastic material.

4. The device of claim 2, wherein said tubular graft is positioned within said tubular stent and coupled thereto.

5. The device of claim 2, wherein said graft comprises a fluoropolymer.

6. The device of claim 5, wherein said fluoropolymer comprises polytetrafluoroethylene.

7. The device of claim 2, wherein said stent has at least one flared end.

8. The device of claim 2, further including a releasable fastening member for maintaining said tubular stent and coaxial graft in a lumen insertable configuration and releasing said lumen insertable configured stent and coaxially positioned into an enlarged configuration once positioned in a lumen.

9. The device of claim 8, wherein said stent and coaxial graft have a length that remains substantially unchanged when the stent and coaxial graft are in either the lumen insertable configuration or said enlarged configuration.

10. The device of claim 2, wherein said coupling member maintains undulation of one helical turn in-phase with undulations of an adjacent helical turn.

11. The device of claim 1, wherein said undulating member comprises stainless steel.

12. The device of claim 1, wherein said undulating member comprises a cobalt chromium alloy.

13. The device of claim 1, wherein said undulating member comprises a platinum/tungsten alloy.

14. The device of claim 1, wherein said undulating member comprises a nickel-titanium alloy.

15. The device of claim 1, wherein adjacent undulations in said undulating member have different amplitudes.

16. The device of claim 1, wherein adjacent undulations in said undulating member have substantially the same amplitude.

17. The device of claim 1, wherein said undulating member is approximately sinusoidal in shape.

18. The device of claim 1, wherein said undulations are approximately U-shaped.

19. The device of claim 1, wherein said undulating member is a wire.

20. The device of claim 1, wherein apexes of undulations of one helical turn are longitudinally spaced from apexes in an adjacent helical turn.

21. The device of claim 1, further including a releasable fastening member maintaining said tubular stent in a lumen insertable configuration and releasing said lumen insertable configured stent into an enlarged configuration once positioned in a lumen.

22. The device of claim 21, wherein said stent has a length that remains substantially unchanged when the stent is in either the lumen insertable configuration or said enlarged configuration.

23. The device of claim 1, wherein said undulations are V-shaped.

24. The device of claim 1, wherein said undulations are ovaloid in shape.

25. The device of claim 1 wherein said undulating member is formed from sheet material.

26. The device of claim 1 wherein said undulating member is formed from tubing.

27. The device of claim 2, wherein said undulating member is formed from a superelastic alloy.

* * * * *